United States Patent [19]

McGhee et al.

[11] Patent Number: 5,260,473
[45] Date of Patent: Nov. 9, 1993

[54] PREPARATION OF URETHANE AND CARBONATE PRODUCTS

[75] Inventors: William D. McGhee, Bridgeton; Dennis P. Riley, Ballwin, both of Mo.

[73] Assignee: Monsanto Company, St. Louis, Mo.

[21] Appl. No.: 976,809

[22] Filed: Nov. 16, 1992

Related U.S. Application Data

[62] Division of Ser. No. 692,857, Apr. 29, 1991, Pat. No. 5,223,638.

[51] Int. Cl.$^5$ .............................. C07C 69/96
[52] U.S. Cl. .................. 558/260; 558/270; 558/271; 558/275; 558/277
[58] Field of Search ................ 558/275, 277

[56] References Cited

U.S. PATENT DOCUMENTS

| | | | |
|---|---|---|---|
| 4,301,087 | 11/1981 | Greene | 558/6 |
| 4,617,281 | 10/1986 | Green | 558/277 |
| 5,200,547 | 4/1993 | Riley et al. | 558/275 |

FOREIGN PATENT DOCUMENTS

0477159A1  3/1992  European Pat. Off.

OTHER PUBLICATIONS

Abstract of JP-56002937, Jan. 13, 1981.
Abstract of JP-57058645, Apr. 8, 1982.
Yoshida, Y. et al., "Novel Synthesis of Carbamate Ester from Carbon Dioxide, Amines, and Alkyl Halides", *Bull. Chem. Soc. Jpn.*, 62, 1534-38 (1989).
Hori, Y. et al., "New Organic Synthesis with DBU: Part 7. Synthesis of Carbonates and Carbamates with Carbon Dioxide Gas as the Starting Material", *Chemistry Express*, vol. 1, No. 4, pp. 224–227 (1986).

*Primary Examiner*—José G. Dees
*Assistant Examiner*—Dwayne C. Jones
*Attorney, Agent, or Firm*—Kenneth D. Goetz

[57] ABSTRACT

The present invention provides a process for preparing urethanes and carbonates from an amine or an alcohol, carbon dioxide and a hydrocarbyl halide. The amine or alcohol is reacted with carbon dioxide in a suitable solvent system and in the presence of an amidine or guanidine base, to form the ammonium carbamate or carbonate salt which is then reacted in a polar aprotic solvent with a hydrocarbyl halide. Polymer products can also be prepared utilizing this process or utilizing the resulting urethanes and carbonates under standard polymerization conditions.

12 Claims, 2 Drawing Sheets

PREPARATION OF URETHANE AND CARBONATE PRODUCTS

CROSS REFERENCE TO RELATED APPLICATION

This application is a divisional of pending application Ser. No. 692,857, filed Apr. 29, 1991 now U.S. Pat. No. 5,187,302.

BACKGROUND OF THE INVENTION

The present invention relates to a process for preparing urethanes and carbonates and, more particularly, relates to a new and useful process for preparing urethanes from amines, carbon dioxide and a hydrocarbyl halide and for preparing carbonates from alcohols, carbon dioxide and a hydrocarbyl halide. The present invention also relates to polymers prepared from such urethanes and/or carbonates.

2. Prior Art

Urethanes and carbonates are typically synthesized by the reaction of a primary amine or an alcohol with phosgene to form an isocyanate or carbonate salt. Thereafter, the isocyanate or carbonate is reacted with an alcohol to form the corresponding urethane or carbonate. Phosgene is very toxic and thus requires very careful handling from a product and worker safety standpoint. Isocyanates are sensitizers and are extremely toxic as well. Preparing urethane and carbonate products without using phosgene and in an economical manner, and preparing urethane products without generating isocyanates would be an achievement of considerable significance in the art.

U.S. Pat. No. 4,467,089 discloses the preparation of certain carbamic acid derivatives (carbonates and carbamate esters) by the simultaneous reaction of a secondary amine and a tertiary amine with carbon dioxide to produce corresponding tertiary amine salts of N-substituted carbamic acid. The secondary and tertiary amines are brought together in equimolar proportions in the presence of excess carbon dioxide under mild conditions. The secondary amine reacts with $CO_2$ in the presence of the tertiary amine to form the corresponding disubstituted tertiary ammonium carbamate salt. The salt is described as being useful as heat activatable delayed action catalysts, especially for use in polyurethane formulations.

Yoshida et al, Bull. Chem. Soc. Jpn., 62, 1534-38 (1989) discloses preparation of urethanes from amines, carbon dioxide and alkyl halides. However, under the reaction conditions specified therein, yields of urethane product are poor as nitrogen derived products are the predominant product.

In Chemistry Express, Vol. 1, No. 4, pp 224-227 (1986), Kinki Chemical Society, Japan, it is disclosed that primary and secondary amines absorb $CO_2$ to form carbamic acid amine salts and that when an equivalent of 1,8-diazabicyclo[5.4.0]undec-7-ene (DBU) is added, additional $CO_2$ is absorbed to form the DBU-carbamate salt. The DBU-carbamate salt when reacted in a nonpolar aprotic solvent with an alkylating agent forms a carbamate ester (urethane). Yield and selectivity of the urethane product are highly dependent on the nature of the alkylating agent. When dibutylamine is reacted with $CO_2$ in the presence of DBU and the resulting DBU-carbamate salt is reacted with butyl chloride as the alkylating agent, a yield of only 17% is realized. With butyl bromide, the yield is 86%. However, when the reaction with butyl bromide was repeated, it was observed that this yield could be achieved only if the reaction was allowed to continue for an extensive period of time, such as from about 18 to about 30 hours. Thus, this reaction, like the reaction disclosed by Yoshida et al, is not commercially practicable.

It has now been discovered that unexpectedly high yields can be achieved in a commercially practicable period of time, i.e. from one-fourth to one-half of the time set forth above, by conducting the reaction in a polar aprotic solvent and in the presence of a strongly basic nitrogen-containing base selected from amidine- and guanidine-type bases.

SUMMARY OF THE INVENTION

The present invention provides a new and useful process for making urethanes and carbonates. The present invention also provides a new and useful process for making polyurethanes and polycarbonates. A preferred embodiment of the present inventive process is a process for making urethanes and carbonates of the following general formula:

wherein $R_1$ represents alkyl, alkenyl, cycloalkyl, cycloalkenyl, aralkyl, and aralkenyl radicals having from 1 to about 22 carbon atoms, provided that $R_1$ is not a tertiary radical of the formula $(R)_3C-$ or $(R)_2C=C(R)-$; A represents a radical selected from the group consisting of $-NR_2R_3$, $NHCH(R_3)COOH$ and $OR_4$ wherein $R$, $R_2$ and $R_3$ independently represent hydrogen and alkyl, alkenyl, cycloalkyl, cycloalkenyl, aralkyl, alkenaryl and alkaryl radicals having from 1 to about 22 carbon atoms, provided that not more than one of $R_2$ and $R_3$ in the formula $-NR_2R_3$ is hydrogen; $R_4$ represents alkyl, alkenyl, cycloalkyl, cycloalkenyl, aralkyl, aralkenyl, alkenaryl, and alkaryl radicals having from 1 to about 22 carbon atoms;

$R_2$ and $R_3$ together with the nitrogen may be bound to form a saturated or unsaturated heterocyclic 5 to 9 membered ring radical, such as morpholino, pyrrolidino, piperidino, and the like. In addition, one of $R_2$ or $R_3$ can be wherein n represents an integer of from 0 to about 8; R is as defined above, $R_1$ is as defined above and $R_5$ represents alkylene radicals, which may be straight-chain or branched, having from 1 to about 22 carbon atoms, i.e., the new and novel urethanes of this invention may be diurethanes. Likewise, $R_4$ can be wherein n represents an integer of from 0 to about 8; $R_1$ and $R_2$ are as defined above, and $R_5$ represents alkylene radicals, which may be straight chain or branched, having from 1 to about 22 carbon atoms, i.e., the new and novel carbonates may be dicarbonates.

The process for preparing the subject urethanes and carbonates is characterized by reacting, in the presence of an amidine- or guanidine-type base, a suitable primary or secondary mono- or polyamine, or a suitable primary, secondary or tertiary mono-alcohol or polyol, with carbon dioxide to form the corresponding carbamate salt or carbonate salt which is then reacted with a hydrocarbyl halide. In order to achieve high yields in a reasonable period of time, the reaction between the salt and the hydrocarbyl halide is carried out in a polar aprotic solvent. Although the reaction between the amine or alcohol and carbon dioxide can be conducted in a variety of solvents, it is preferred to conduct such reaction in the polar aprotic solvent as well, primarily for convenience to avoid isolation of the salt.

The present invention is based on nucleophilic attack on the hydrocarbyl halide by carbamate anions premade from $CO_2$, a primary or secondary mono- or polyamine and a tertiary amine base, or by nucleophilic attack of carbonate anions pre-made from $CO_2$, a primary, secondary or tertiary mono-alcohol or polyol and a tertiary amine base. Urethane products made in accordance with the present invention are useful in specialty chemical applications, such as, for example, as cross-linking agents. Carbonate products made in accordance with this invention are useful in preparing polymers which are useful in shatter-resistant optical lenses, face shields and windows.

DETAILED DESCRIPTION OF THE INVENTION

The urethanes are prepared in accordance with the present invention by bringing into reactive contact a suitable primary or secondary mono- or diamine, or a mixture thereof, carbon dioxide and an amidine or guanidine base in a confined zone, such as a reactor, to prepare the corresponding ammonium carbamate salt. Similarly, the carbonates are prepared in accordance with the present invention by bringing into reactive contact a suitable primary, secondary or tertiary monoalcohol or diol, or polyol or a mixture thereof, carbon dioxide and a base in a confined zone, such as a reactor, to prepare the corresponding carbonate salt. Preferably the amines or alcohols are in solution and the carbon dioxide is bubbled through the solution. The reaction proceeds without the need of elevated pressure or temperatures in a slightly exothermic reaction to give either the ammonium salt of the corresponding carbamate anion or the salt of the corresponding carbonate anion. Use of at least an essentially stoichiometric amount of the base during the reaction with carbon dioxide provides the desired urethane and carbonate products.

The ammonium salt of the carbamate anion is prepared in solution in the presence of the amidine-or guanidine-type base. The guanidine as well as certain amidine salts of the carbamate anions are novel and represent another aspect of the present invention. The use of a base shifts the equilibrium toward the production of the carbamate anions. Where the reaction between the primary or secondary amine is carried out in the presence of a base, the reaction may be represented by the equation (1). The resulting ammonium carbamate salt solutions are normally homogeneous.

$$R_2R_3NH + Base + CO_2 = R_2R_3NCO^-_2 \, HBase^+ \quad (1)$$

Equation (2) shows the results of the addition of the carbamate anion to a hydrocarbyl halide.

$$R_2R_3NCO_2^- \, HBase^+ + R_1 \, Halide \quad (2)$$

$$R_2R_3NCO_2—R_1 + HBase^+ \, Halide^-$$

In order to conduct the reaction with reasonable rates and commercially practicable yields, addition of the carbamate anion to the hydrocarbyl halide is performed in a polar aprotic solvent. Normally, the reaction, when conducted in a polar aprotic solvent, proceeds smoothly under mild conditions, e.g. at 25° C. and 110 psi carbon dioxide pressure, to give the corresponding product in high yields.

Suitable primary or secondary amines used to prepare the carbamate esters in accordance with the present invention include amino acids such as glycine, aspartic acid and the like, amines represented by the following general formula:

$$R_2R_3NH,$$

wherein $R_2$ and $R_3$ independently represent hydrogen, provided that no more than one of $R_2$ and $R_3$ is hydrogen, alkyl, alkenyl, cycloalkyl, cycloalkenyl, aryl, aralkyl, aralkenyl, alkenaryl and alkaryl radicals having from 1 to about 22 carbon atoms, which radicals can be straight-chain or branched; and a radical represented by the formula $—(—R_5—)_n—NHR$ wherein R represents radicals as defined above for $R_2$, $R_5$ represents alkylene radicals having from about 1 to about 22 carbon atoms and n represents an integer of from 0 to about 8. Examples of $R_2$ and $R_3$ include methyl, ethyl, n-propyl, isopropyl, n-butyl, isobutyl, t-butyl, n-pentyl, isopentyl, n-hexyl, n-octyl, phenyl, benzyl, and the like. Specific examples of such suitable amines include N-ethyl(benzyl)amine, N,N-diallyamine; N,N-diethylamine; N-cyclohexylamine; N,N'-dimethylhexamethylene amine and the like. In addition, $R_2$ and $R_3$ together with the nitrogen can be bound to form a saturated or unsaturated 5 to 9 membered ring radical. Examples of such ring radicals include morpholino, pyrrolidino, piperidino, and the like. Suitable amines also include polyamines such as, for example, tetraethylene pentamine, diethylene triamine, triethylene tetramine and pentaethylene hexamine and the like, as well as amino acids such as alanine, arginine, asparagine, aspartic acid, cysteine, glutamine glutamic acid, glycine, histidine, isoleucine, leucine, lysine, methionine, phenylalanine, proline, serine, threonine, tryptophan, tyrosine, valine, t-butyl glycine, ornithine, norleucine and the like, including β-amino acids and homo-β-amino acids.

The amine reacts with $CO_2$ to reversibly form the corresponding ammonium carbamate salt. To shift the equilibrium reaction more favorably to the ammonium carbamate salt, a strongly basic nitrogen-containing base is added. Such nitrogen bases include amidines (e.g., DBU, 1,8-diazabicyclo[5.4.0]undec-7-ene, etc.) and guanidines (e.g., cyclohexyltetramethylguanidine, cyclohexyltetraethylguanidine, and the like).

The salt of the carbonate anion can be prepared in solution in the presence of a nitrogen-containing base selected from amidines and guanidines. The guanidine as well as certain amidine salts of the carbonate anions are novel and represent another aspect of the present invention. The reaction between the alcohol and carbon dioxide can be represented by the equation (3). The resulting carbonate salt solutions are normally homogeneous.

$$R_7R_8R_9COH + Base + CO_2 = R_7R_8R_9COCO_2^- \, HBase^+ \quad (3)$$

Equation (4) shows the results of the addition of the complex of equation 3 to a hydrocarbyl halide.

$$R_7R_8R_9COCO_2^- \, HBase^+ + R_4 \, Halide \quad (4)$$

$$R_7R_8R_9COCO_2 R_4 + HBase^+ \, Halide^-$$

Typically, the reaction, when conducted in a polar aprotic solvent, proceeds smoothly under mild conditions, e.g., at 25° C. and 110 psi $CO_2$ pressure, to give the corresponding product in high yield.

Suitable primary, secondary and tertiary alcohols used to prepare the carbamate esters in accordance with the present invention can be represented by the following general formula:

$$R_7R_8R_9COH$$

wherein $R_7$, $R_8$, and $R_9$ independently represent hydrogen, and alkyl, alkenyl, cycloalkyl, cycloalkenyl, aralkyl, aralkenyl, alkenaryl and alkaryl radicals having from 1 to about 22 carbon atoms, which radicals can be straight-chain or branched; a radical represented by the formula $-(-R_5-)_n-OH$ wherein $R_5$ and n are as defined above; or when taken together along with C form an aromatic ring structure. Examples of $R_7$, $R_8$, and $R_9$ include methyl, ethyl, n-propyl, isopropyl, n-butyl, isobutyl, t-butyl, n-pentyl, isopentyl, n-hexyl, n-octyl, benzyl, and the like. Specific examples of suitable alcohols include benzyl alcohol, cyclohexanol, ethanol, n-butanol, isopropanol and the like. Suitable alcohols also include diols and polyols such as, for example, ethylene glycol, sorbitol, pentaerythritol and the like.

An advantage of the present process is that the reaction between the amine or the alcohol and $CO_2$ proceeds under mild temperature and pressure. Room temperature and a pressure of 110 psi $CO_2$ are suitable and are preferred. However, if desired, the reaction can be carried out between about 25° C. and about 150° C. under a $CO_2$ pressure in a range of from about 2 psi to about 400 psi, such as from about 10 psi to about 200 psi. A preferred temperature range is from about 30° C. to about 125° C., such as from about 35° C. to about 80° C.

Hydrocarbyl halides suitable for use in the present invention can be represented by the formula $R_1X$ wherein $R_1$ represents alkyl, alkenyl, cycloalkyl, cycloalkenyl, aralkyl and aralkenyl radicals having from 1 to about 22 carbon atoms, provided that $R_1$ is not a tertiary radical of the formula $(R)_3C-$ or $(R)_2C=C(R)-$ and X represents Cl, Br, I and F. Examples of such hydrocarbyl halide include alkyl, cycloalkyl, alkenyl, aralkyl halides. Specific examples of such halides include methyl chloride, methyl iodide, ethyl bromide, n-butyl bromide, n-butyl chloride, iso-butyl chloride, amyl chloride, n-octyl chloride, benzyl bromide, benzyl chloride, (2-naphthyl)methyl chloride, 3-chlorocyclohexene, 3-chlorocyclohexane, 2-methyl allyl chloride, 4-chloro-2-butene and the like. Hydrocarbyl dihalides and polyhalides may also be used. For example, 1,4-dichloro-2-butene, 1,4-dichlorobutane, dichloro-p-xylene, and the like, may be utilized. The present invention is also applicable to formation of cyclic carbamates and carbonates wherein a suitable alcohol or amine, as described above, containing a suitable leaving group such as a halide is reacted with $CO_2$ as set forth herein, in the presence of an amidine or guanidine base.

The reaction between the salt and the hydrocarbyl halide is carried out in a suitable polar aprotic organic solvent. As utilized herein, the phrase "polar aprotic organic solvent" means an aprotic organic solvent having a dielectric constant of greater than about 10ε as reported in Reichardt, C., "Solvents and Solvent Effects in Organic Chemistry," 2nd ed., VCH Verlagsgesellschaft, Weinheim, (1988), Table A-1, utilizing toluene (2.38ε) and tetrahydrofuran (7.58ε), both at 20° C., as standards. Other methods for determining dielectric constants are known and suitable solvents are those having a dielectric constant greater than that of tetrahydrofuran utilizing any of such methods. Examples of suitable solvents include acetonitrile, N-methyl pyrrolidone, dimethylformamide, dimethylsulfoxide, and the like, as well as mixtures thereof. Preferred solvents are acetonitrile and DMSO. Although not specifically required, it is preferred to utilize these same solvents to carry out the reaction between the amine or alcohol and carbon dioxide in order to avoid the step of isolating the salt. However, this reaction can also be conducted in other organic solvents which are not polar aprotic solvents, such as, for example, THF, methylene chloride and the like.

To obtain high selectivity for urethanes over amine products (oxygen vs. nitrogen attack) and high selectivity for carbonates over ethers, the anion is stabilized by the use of an essentially stoichiometric amount of a base. The term base as utilized herein refers to a base utilized in addition to the reactant amine or alcohol. This is the strongly basic nitrogen-containing base, e.g., a sterically-hindered tertiary amine base. Addition of the premade carbamate, or carbonate, anion under carbon dioxide pressure to a solution of a hydrocarbyl halide in a suitable polar aprotic solvent gives high yields and selectivities of urethanes and carbonates and with high rates. The selection of the base in the formation of the carbamate or carbonate is important in order to obtain higher selectivities and thus higher yields. The base preferably has one of the general structures shown below.

guanidine   amidine

These bases are known in the art and several are commercially available. Examples of such bases include 1,5-diazabicyclo[4.3.0]non-5-ene (DBN); 1,8-diazabicyclo-[5.4.0]undec-7-ene (DBU); 7-methyl-1,5,7-triazabicyclo[4.4.0]dec-5-ene (MTBD); cycohexyl tetrabutyl guanidine (CyTBG) and cyclohexyl tetramethyl guanidine (CyTMG). Preferably, the molar ratio of base to the amine or alcohol starting materials will be within the range of from about 1:1 to about 10:1. A preferred molar ratio is in the range of from about 1:1 to about 1.5:1. A most preferred molar ratio is 1:1. The rate of reaction between the carbamate or carbonate salts and the hydrocarbyl halide can be increased by utilizing excess, up to about 2 moles per mole of carbamate or carbonate, hydrocarbyl halide. It is believed that use of such excess hydrocarbyl halide facilitates reaction conditions which are pseudo-first order as opposed to second order. Thus, in order to render the present process more commercially practicable, it is preferred to use an excess of such hydrocarbyl halide.

It is contemplated that mixtures of alcohols and mixtures of amines can be utilized effectively in the process of the present invention. Furthermore, it is contemplated that compounds which include both alcohol and amine functional groups, e.g., diethanolamine, can be utilized effectively in the process of the present invention. In addition, it is contemplated that an alcohol/amine mixture, e.g., a mixture of N-benzyl-N-ethyl amine and benzyl alcohol, can be utilized effectively in the process of the present invention. It is also contemplated that carbon disulfide can be utilized in place of carbon dioxide to produce the corresponding dithiocarbamates and dithiocarbonates.

Contemplated equivalents of the general formulas set forth above for the alcohols, amines and hydrocarbyl halides are compounds otherwise corresponding thereto and having the same general properties wherein one or more of the various R groups are simple variations of the substituents as defined therein, e.g., wherein R is a higher alkyl group or includes a substituent such as, for example, a halide, amino substituents, hydroxy substituents and the like. In addition, where a substituent is designated as, or can be, a hydrogen, the exact chemical nature of a substituent which is other than hydrogen at that position is not critical so long as it does not adversely affect the overall synthesis procedure. For example, where the above-specified alcohols and amines are mono- and difunctional alcohols and amines, equivalents thereof which are suitable for use in the present invention include polyols and polyamines. Where a halide is considered a leaving group, for example, as in the hydrocarbyl halide, other leaving groups such as tosyl, mesylate, triflate and the like, which are all well known in the art, are contemplated equivalents.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrated examples wherein parts and percentages are given on a molar basis unless otherwise specified.

All amines and alcohols used in the following examples were obtained either from Aldrich Chemical Company or Kodak Chemical Company and were used as received. Anhydrous solvents under nitrogen were purchased from Aldrich Chemical Co. DBN (1,5-diazabicyclo[4.3.0]non-5-ene and DBU (1,8-diazabicyclo[5.4.0]undec-7-ene, were also purchased from Aldrich Chemical Co.; MTBD (7-methyl-1,5,7-triazabicyclo[4.4.0]dec-5-ene was obtained from Fluka; CyTMG (cyclohexyl tetramethyl guanidine), as well as the other cyclohexyl tetraalkyl guanidines were synthesized according to the general procedure set forth in Bredereck H.; Bredereck K. *Chem Ber*, 94, (1961) 2278–2295. Thus, N-cyclohexyl-N',N',N'',N''-tetrabutylguanidine was synthesized according to the following procedure:

In a 3-1, 3-neck flask equipped with a dropping funnel, mechanical stirrer, and $N_2$-bubbler, 1 mole tetrabutylurea was added and dissolved in 500 mL toluene. One mole $POCl_3$ was added dropwise over a 30-minute period. The reaction was allowed to stir for 5 h at room temperature and 2.2 mole cyclohexylamine was added dropwise over a 30 minute period. The reaction was allowed to stir at room temperature for 20 h. After this period of time, the reaction was quenched with 500 mL of water. The mixture was allowed to stir vigorously for 15 minutes and then the top toluene layer was discarded. Excess solid NaOH was added to the bottom layer until two new layers were formed. The solid was filtered off and the two layers of the filtrate were separated. The bottom layer was discarded and the process was repeated with the top layer. Again, the mixture was filtered and the layers were separated. The bottom layer was discarded and the top layer was dissolved in diethyl ether. The ether solution was dried over $Na_2CO_3$, filtered and concentrated. The base was purified by distillation.

Gas chromatographic analysis was performed on a Varian Model 3400 gas chromatograph with a model 8000 auto sampler using a 30 meter Megabore DB-1 (3μm) J & W Scientific column. Urethane products were purified and were identified by $^1H$ NMR, $^{13}C$ NMR, mass spectroscopy, IR, and elemental analysis. Nuclear Magnetic Resonance spectra were obtained on Varian VXR-300 or VXR-400 spectrometers. Mass spectra were obtained by FAB or by chemical ionization techniques using isobutane as reagent gas. Infrared spectra were obtained on a Nicolet FTIR. Molecular weight determinations of polymers were obtained on GPC Waters System comprised of a WISP 700 autosampler, 600E system controller, 500521, $10^3Å$, $10^4Å$ and $10^5Å$ gel permeation columns in series, 410 Differential Refractometer and a Maxima 820 workstation. Molecular weights are based on polystyrene standards.

EXAMPLE 1

This example illustrates N-butyl-benzylcarbamate generation utilizing a variety of bases and demonstrates that an amidine- or guanidine-type base is required. The bases utilized in Rxn #s 4–15 are amidine or guanidine bases whereas those of Rxn #s 1–3 are not. General procedure: A Fischer Porter bottle was charged with 1.46 g (0.02 mol) butyl amine, (0.027 mol) base, 154 mg (0.001mol) biphenyl as internal G.C. standard, and 20 mL $CH_3CN$. The Fischer-Porter bottle was attached to a pressure head and at room temperature with stirring was added 80 psig carbon dioxide. Addition of $CO_2$ resulted in an exothermic reaction with a rise in temperature to ca. 40° C. Into a second Fischer-Porter bottle was added 10.12 g (0.08 mol) benzyl chloride in 10 mL $CH_3CN$. This mixture was attached to a pressure head and 80 psig carbon dioxide was added above the solution. After 1 h the benzyl chloride solution was added all at once under 80 psig $CO_2$ to the pre-formed carbamate anion solution generated in the first Fischer-Porter bottle. After addition the reaction mixture was warmed to 55° C. Aliquots were taken periodically and were diluted with diethyl ether, Cl⁻⁺H Base filtered off, and G.C. yields calculated. The results of this study ar given in Table 1.

TABLE 1

$$BuNH_2 + CO_2 + Base \xrightarrow[PhCH_2Cl]{CH_3CN} BuNHCO_2CH_2Ph$$

| Rxn # | Base[1] | % Urethane G.C. Yield | % Nitrogen derived Products[2] |
|---|---|---|---|
| 1 | Proton Sponge | 0 | 63 |
| 2 | BuNH₂ | 2 | 77 |
| 3 | PMP | 7 | 92.5 |
| 4 | n-BuTEG | 45 | 24 |
| 5 | t-BuDEF | 48 | 34 |
| 6 | TEG | 50 | 17 |
| 7 | TMG | 62 | 22 |
| 8 | DBU | 69 | 18 |
| 9 | MTDB | 86 | 14 |
| 10 | t-BuDMA | 87 | 18 |
| 11 | CyTEG | 92 | 14 |
| 12 | t-BuTEG | 92 | 13 |
| 13 | CyTMG | 94 | 9 |
| 14 | CyTBG | 97 | 6 |

All reactions run at 55° C. under 80 psig carbon dioxide pressure and run to completion based on butyl amine.
G.C. yields determined using biphenyl as internal standard.
[1]Proton Sponge = N,N,N'N'-tetramethyl-1,8-naphthalenediamine.
PMP = 1,2,2,6,6-pentamethylpiperadine.
N—BuTEG - N-butyl-N',N',N'',N''-tetraethylguanidine.
t-BuDEF = N-t-butyl-N',N'-diethylformamidine.
TEG = N,N,N',N'-tetraethylguanidine.
TMG - N,N,N',N'-tetramethylguanidine.
DBU - 1,8-diazabicyclo[5.4.0]undec-7-ene.
MTDB = 7-methyl-1,5,7-triazabicyclo[4.4.0]dec-5-ene.
t-BuDMA = N-t-butyl-N',N'-dimethylacetamidine.
CyTEG = N-cyclohexyl-N',N',N'',N''-tetraethylguanidine.
t-BuTEG = N-t-butyl-N',N',N'',N''-tetraethylguanidine.
CyTMG = N-cyclohexyl-N',N',N'',N''-tetramethylguanidine.
CyTEG = N-cyclohexyl-N',N',N'',N''-tetraethylguanidine.
CyTBG = N-cyclohexyl-N',N',N'',N''-tetrabutylguanidine.
[2]Nitrogen derived products include, N-butyl-N-benzylamine, N-butyl-N,N-dibenzyl amine and N-butyl-N-benzyl benzylcarbamate (secondary product derived from the N-butyl-N-benzyl amine generated). A small amount of dibenzylcarbonate resulting from trace amounts of water in reagents was also detected by G.C.

EXAMPLE 2

This example illustrates N-butyl-benzylcarbamate generation utilizing a variety of polar aprotic solvents. General procedure: A Fischer Porter bottle was charged with 1.46 g (0.02 mol) butyl amine, (0.027 mol) base (either 1,8-diazabicyclo[5.4.0]undec-7-ene or N-cyclohexyl-N',N',N'',N''-tetramethylguanidine), 154 mg (0.001mol) biphenyl as internal G.C. standard, and 20 mL solvent. The Fischer-Porter bottle was attached to a pressure head and at room temperature with stirring was added 80 psig carbon dioxide. Addition of CO₂ resulted in an exothermic reaction with a rise in temperature to ca. 40° C. Into a second Fischer-Porter bottle was added 10.12 g (0.08 mol) benzyl chloride in 10 mL solvent. This mixture was attached to a pressure head and 80 psig carbon dioxide was added above the solution. After 1 h the benzyl chloride solution was added all at once under 80 psig CO₂ to the pre-formed carbamate anion solution generated in the first Fischer-Porter bottle. After addition the reaction mixture was warmed to 55° C. Aliquots were taken periodically and were diluted with diethyl ether, Cl⁻⁺H Base filtered off, and G.C. yields calculated. The results of this study are given in Table 2.

TABLE 2

$$BuNH_2 + CO_2 + Base \xrightarrow[PhCH_2Cl]{Solvent} BuNHCO_2CH_2Ph$$

| Rxn # | Base[1] | Solvent[2] | % Urethane G.C. Yield | % Nitrogen derived Products[3] |
|---|---|---|---|---|
| 1 | DBU | N—MF | 35 | 46 |
| 2 | DBU | DMF | 57 | 8 |
| 3 | DBU | N—MP | 59 | 18 |
| 4 | DBU | CH₃CN | 69 | 19 |
| 5 | DBU | Sulfolane | 69 | 28 |
| 6 | CyTMG | Toluene | 84 | 9 |
| 7 | CyTMG | N—MP | 59 | 9 |
| 8 | CyTMG | CH₃CN | 94 | 9 |
| 9 | CyTMG | TMU | 70 | 15 |
| 10 | CyTMG | Sulfolane | 89 | 11 |

All reactions run at 55° C. under 80 psig carbon dioxide pressure and run to completion based on butyl amine.
G.C. yields determined using biphenyl as internal standard.
[1]DBU = 1,8-diazabicyclo[5.4.0]undec-7-ene.
CyTMG = N-cyclohexyl-N',N',N'',N''-tetramethylguanidine.
[2]N—MF = N-methylformamide.
DMF = N,N-dimethylformamide.
N—MP = 1-methyl-2-pyrrolidinone.
TMU = tetramethylurea.
[3]Nitrogen derived products include, N-butyl-N-benzyl amine, N-butylN,N-dibenzyl amine and N-butyl-N-benzyl benzylcarbamate (secondary product derived from the N-butyl-N-benzyl amine generated). A small amount of dibenzyl carbonate resulting from trace amounts of water in reagents was also detected by G.C.

The following examples, namely Examples 3–15, illustrate a variety of urethanes prepared according to the teachings of the present invention. For comparison purposes, a summary of these examples is set forth in Table 3.

Example 3

N,N-dibutyl benzylcarbamate (1)

A Fischer Porter bottle was charged with 2.58 g (0.02 mol) dibutyl amine, 3.94 g (0.02 mol) N-cyclohexyl-N',N',N'',N''-tetramethylguanidine, 154 mg (0.001 mol) biphenyl as internal G.C. standard, and 20 mL CH₃CN. The Fischer-Porter bottle was attached to a pressure head and at room temperature with stirring was added 80 psig carbon dioxide. Addition of CO₂ resulted in an exothermic reaction with a rise in temperature to ca. 40° C. Into a second Fischer-Porter bottle was added 10.12 g (0.08 mol) benzyl chloride in 10 mL CH₃CN. This mixture was attached to a pressure head and 80 psig carbon dioxide was added above the solution. After 1 h the benzyl chloride solution was added all at once under 80 psig CO₂ to the pre-formed carbamate anion solution generated in the first Fischer-Porter bottle. After addition the reaction mixture was warmed to 40° C. for 3 h. After this time the reaction mixture was allowed to cool to room temperature and then the pressure was released. An aliquot was taken, diluted with diethyl ether, Cl⁻⁺HCyTMG precipitated from solution and was filtered off, and by G.C. analysis a 95% yield of urethane was calculated. The crude material was poured into 100 mL ethyl acetate and extracted with 2×100 mL 0.5 M aq. HCl followed by 100 mL brine. The organic layer was dried over Na₂CO₃, filtered and concentrated leaving a light yellow oil. This oil was chromatographed on silica gel using first 100% hexane (to remove excess benzyl chloride and internal G.C. standard) and then with 100% CH₂Cl₂. The O-benzyl carbamate product, 1, was isolated as a clear oil (3.38 g, 64%). Oil ¹H NMR (CDCl₃) δ 7.39–7.30 (overlapping m, 5H), 5.17 (s, 2H), 3.27 (br, 4H), 1.55 (br, 4H), 1.33 (br m, 4H), 0.94 (br, 6H). ¹³C{¹H} NMR (CDCl₃) δ 156.7, 137.7, 128.9, 128.3, 128.2, 67.2, (47.8, 47.2), (31.4, 30.8), 20.5, 14.4. IR (film) 1703; MS FAB m/z=264 (MH=). Anal. Calcd.: C, 72.97; H, 9.57; N, 5.32. Found: C, 73.22; H, 9.35; N, 5.45.

EXAMPLE 4

N,N-diethyl benzylcarbamate (2)

Procedures as described in synthesis of 1. A G.C. yield of 95% was calculated and a 47% isolated yield of N,N-diethyl benzylcarbamate, 2 resulted. Oil. $^1$H NMR (CDCl$_3$) δ 7.35-7.25 (overlapping m, 5H), 5.12 (s, 2H), 3.29 (br q, J=6.4 Hz, 4H), 1.15 (t, J=6.9 Hz, 6H). $^{13}$C {$^1$H} NMR (CDCl$_3$) δ 155.7, 137.1, 128.4, 127.7, 127.6, 66.7, 41.6 (br), 13.8 (br). IR (film) 1700; MS (EI) m/z=207 (M+).

EXAMPLE 5

N-butyl benzyl carbamate (3)

A Fischer Porter bottle was charged with 1.46 g (0.02 mol) butyl amine, 5.32 g (0.027 mol) N-cyclohexyl-N',N',N'',N''-tetramethylguanidine, 154 mg (0.001 mol) biphenyl as internal G.C. standard, and 20 mL CH$_3$CN. The Fischer-Porter bottle was attached to a pressure head and at room temperature with stirring was added 80 psig carbon dioxide. Addition of CO$_2$ resulted in an exothermic reaction with a rise in temperature to ca. 40° C. Into a second Fischer-Porter bottle was added 10.12 g (0.08 mol) benzyl chloride in 10 mL CH$_3$CN. This mixture was attached to a pressure head and 80 psig carbon dioxide was added above the solution. After 1h the benzyl chloride solution was added all at once under 80 psig CO$_2$ to the pre-formed carbamate anion solution generated in the first Fischer-Porter bottle. After addition the reaction mixture was warmed to 55° C. for 18 h. After this time the reaction mixture was allowed to cool to room temperature and then the pressure was released. An aliquot was taken, diluted with diethyl ether, Cl$^-$+HCyTMG precipitated from solution and was filtered off, and by G.C. analysis a 95% yield of urethane was calculated. The crude material was poured into 100 mL ethyl acetate and extracted with 2×100 mL 0.5 M aq. HCl followed by 100 mL brine. The organic layer was dried over Na$_2$CO$_3$, filtered and concentrated leaving a light yellow oil. This oil was chromatographed on silica gel using first 100% hexane (to remove excess benzyl chloride and internal G.C. standard) and then with 100% CH$_2$Cl$_2$. The O-benzyl carbamate product, 3, was isolated as a clear oil (2.64 g, 64%). Oil. $^1$H NMR (CDCl$_3$) δ 7.40-7.34 (overlapping m, 5H), 5.14 (s, 2H), 4.9 (br s, N—H), 3.21 (br q, J=5.1 Hz, 2H), 1.51 (m, 2H), 1.38 (m, 2H), 0.96 (t, J=7.2 Hz, 3H). $^{13}$C {$^1$H} NMR (CDCl$_3$) δ 156.4, 136.6, 128.4, 128.2, 127.9, 66.4, 40.7, 31.9, 19.7, 13.6. IR (film) 3337, 1701; MS m/z=(MH+).

EXAMPLE 6

N-sec-butyl benzyl carbamate (4)

Procedures as described in synthesis of 3. A G.C. yield of 89% was calculated and a 44% isolated yield of N-s-butyl benzylcarbamate, 4 resulted. m.p. 49-50.5 °C. $^1$H NMR (CDCl$_3$) δ 7.4-7.30 (overlapping m, 5H), 5.14 (s, 2H), 4.6 (br s, N—H), 3.69 (m, 1H), 1.50 (quintet, J=7 Hz, 2H), 1.17 (d, J=6.6 Hz, 3H), 0.95 (t, J=7.4 Hz, 3H). $^{13}$C {$^1$H} NMR (CDCl$_3$) δ 155.8, 136.7, 128.4, 128.2, 127.9, 66.4, 48.4, 29.8, 20.7, 10.2. IR (CHCl$_3$) 3441, 1713; MS (EI) m/z=207 (M+). Anal. Calcd.: C, 69.54; H, 8.27; N, 6.76. Found: C, 69.71; H, 8.49; N, 6.87.

EXAMPLE 7

N-tert-butyl benzyl carbamate (5)

Procedures as described in synthesis of 3. A G.C. yield of 90% was calculated and a 41% isolated yield of N-t-butyl benzylcarbamate, 5 resulted. Oil. $^1$H NMR (CDCl$_3$) δ 7.38-7.32 (overlapping m, 5H), 5.09 (s, 2H), 4.9 (br, N—H), 1.36 (s, 9H). $^{13}$C {$^1$H} NMR (CDCl$_3$) δ 155.3, 137.4, 129.0, 128.6, 128.5, 66.5, 50.8, 29.5. IR (film) 3346, 1711 (literature 1710); MS (EI) m/z=207 (M+). Anal. Calcd.: C, 69.54; H, 8.27; N, 6.76. Found: C, 69.53; H, 8.14; N, 6.97.

EXAMPLE 8

N-octyl benzylcarbamate (6)

Procedures as described in synthesis of 3. A G.C. yield of 99.5% was calculated and a 53% isolated yield of N-octyl benzylcarbamate, 6 resulted after crystallization from hexane. m.p. 32-33° C. $^1$H NMR (CDCl$_3$) δ 7.41-7.29 (overlapping m, 5H), 5.08 (s, 2H), 4.77 (s, N—H), 3.17 (q, J=6.7 Hz, 2H), 1.48 (m, 2H), 1.26 (overlapping m, 10H), 0.87 (t, J=6.7 Hz, 3H). $^{13}$C {$^1$H} NMR (CDCl$_3$) δ 156.4, 136.7, 128.5, 128.1, 128.0, 66.6, 41.1, 31.8, 30.0, 29.3, 29.2, 26.7, 22.6, 14.0. IR (CHCl$_3$) 3451, 1713; MS m/z=(MH+). Anal. Calcd.: C, 72.97; H, 9.57; N, 5.32. Found: C, 72.86; H, 9.51; N, 5.63.

EXAMPLE 9

N-cyclohexyl benzylcarbamate (7)

Procedures as described in synthesis of 3. A G.C. yield of 97% was calculated and a 50% isolated yield of N-cyclohexyl benzylcarbamate, 7 resulted after crystallization from hot hexane. m.p. 93-94.5.C (literature, m.p. 93-94 C). $^1$H NMR (CDCl$_3$) δ 7.40-7.30 (overlapping m, 5H), 5.13 (s, 2H), 4.7 (br, N—H), 3.54 (m, 1H), 1.99-1.1 (cyclohexyl, 10H). $^{13}$C ($^1$H) NMR (CDCl$_3$) δ 155.5, 136.7, 128.5, 128.1, 128.0, 66.4, 49.9, 33.4, 25.5, 24.7. IR (CHCl$_3$) 3441, 1711; MS (EI) m/z=233 (M+). Anal . Calcd.: C, 72.07; H, 8.21; N, 6.00. Found: C, 72.45; H, 8.36; N, 5.98.

EXAMPLE 10

N-cycloyolohexanemethyl benzyloarbamate (8)

Procedures as described in synthesis of 3. A G.C. yield of 105% was calculated and a 76% isolated yield of N-cyclohexanemethyl benzylcarbamate, 8 resulted after crystallization from hot hexane. m.p. 58.5-61° C. $^1$H NMR (CDCl$_3$) δ 7.4-7.3 (overlapping m, 5H), 5.13 (s, 2H), 4.90 (br, N—H), 3.07 (t, J=6.5 Hz, 2H), 1.8-0.9 (overlapping m, 11H). $^{13}$C {$^1$H} NMR (CDCl$_3$) δ 157.1, 137.3, 129.0, 128.6, 128.5, 67.1, 47.9, 38.8, 31.2, 26.9, 26.3. IR (CHCl$_3$) 3455, 1713; MS m/z=248 (MH+). Anal. Calcd.: C, 72.84; H, 8.56; N, 5.66. Found: C, 72.84; H, 8.54; N, 5.63.

EXAMPLE 11

N-phenyl benzylcarbamate (9)

Procedures as described in synthesis of 3. A G.C. yield of 90% was calculated and a 64% isolated yield of N-phenyl benzylcarbamate, 9 resulted after crystallization from ether/hexane. m.p. 79-80.5° C. $^1$H NMR (CDCl$_3$) δ 7.47-7.33 (overlapping m, 8H), 7.12 (t, J=7.3 Hz, 2H), 6.81 (br, N—H), 5.25 (s, 2H). $^{13}$C {$^1$H} NMR (CDCl$_3$) δ 153.9, 138.3, 136.6, 129.6, 129.2, 128.9, 124.1, 119.3, 67.6. IR (CHCl₃) 3435, 1734; MS (EI) m/z=227 (M+). Anal. Calcd.: C, 73.99; H, 5.77; N, 6.16. Found: C, 73.84; H, 5.80; N, 6.22.

EXAMPLE 12

Tris-benzyl carbamate of N'N',N''-bis(ethylene diamine) (10)

A Fischer porter bottle was charged with 1.03 g (0.01 mol) bis-ethylene tri-amine, 7.39 g (0.0375 mol) N-cyclohexyl-N',N',N'',N'''-tetramethylguanidine, and 20 mL CH₃CN. The Fischer-Porter bottle was attached to a pressure head and at room temperature with stirring was added 80 psig carbon dioxide. Addition of CO₂ resulted in an exothermic reaction with a rise in temperature to ca. 40° C. Into a second Fischer-Porter bottle was added 11.48 g (0.09 mol) benzyl chloride in 10 mL CH₃CN. This mixture was attached to a pressure head and 80 psig carbon dioxide was added above the solution. After 1 h the benzyl chloride solution was added all at once under 80 psig CO₂ to the pre-formed carbamate anion solution generated in the first Fischer-Porter bottle. After addition the reaction mixture was warmed to 55° C. for 18 h. After this time the reaction mixture was allowed to cool to room temperature and then the pressure was released. The crude material was poured into 100 mL ethyl acetate and extracted with 2×100 mL 0.5 M aq. HCl followed by 100 mL brine. The organic layer was dried over MgSO₄, filtered and concentrated. The residue was dissolved in hexane and upon cooling a solid precipitated. After recrystallization from ethyl acetate/hexane an isolated yield of 53% (2.7 g) of the tricarbamate 10 resulted. m.p. 67–68° C. ¹H NMR (CDCl₃) 7.4–7.3 (overlapping m, 15H), 5.5 (br, N—H, 1H), 5.1 (br, N—H, 1H), 5.1 (s, 6H), 3.5–3.3 (overlapping br m, 8H). ¹³C{¹H} NMR (CDCl₃) 157.4, 157.3 (br), 137.1 (br), 136.8, 129.1, 129.0, 128.7, 128.6, 128.5, 68.1, 67.2, 48.3 (br), 40.5 (br). IR (CHCl₃) 3451, 1711; MS (thermal spray) m/z=506 (MH+). Anal. Calcd.: C, 66.52; H, 6.18; N, 8.31. Found: C, 66.60; H, 6.35;, N, 8.30.

EXAMPLE 13

4,4'-methylene-bis(cyclohexyl)-bis-(benxylcarbamate) (11)

A Fischer Porter bottle was charged with 2.1 g (0.01 mol) 4,4'-methylenebis(cyclohexylamine), 4.14 g (0.021 mol) N-cyclohexyl-N',N',N'',N'''-tetramethylguanidine, and 20 mL 1-methyl-2-pyrrolidinone (N-MP). The Fischer-Porter bottle was attached to a pressure head and at room temperature with stirring was added 80 psig carbon dioxide. Addition of CO₂ resulted in an exothermic reaction with a rise in temperature to ca. 40° C. Into a second Fischer-Porter bottle was added 5.06 g (0.04 mol) benzyl chloride in 10 mL N-MP. This mixture was attached to a pressure head and 80 psig carbon dioxide was added above the solution. After 1 h the benzyl chloride solution was added all at once under 80 psig CO₂ to the pre-formed carbamate anion solution generated in the first Fischer-Porter bottle. After addition the reaction mixture was warmed to 55° C. for 16 h. After this time the reaction mixture was allowed to cool to room temperature and then the pressure was released. The crude material was poured into 200 mL H₂O and a white precipitate formed. This white material was collected by filtration and was washed with water followed by air drying at room temperature overnight giving 3.63 g (78%) of the dicarbamate 11. IR (CHCl₃) 3441, 1713. Anal. Calcd.: C, 72.77; H, 8.0; N, 5.85. Found: C, 72.79; H, 8.16; N, 5.94.

EXAMPLE 14

TAN-tribenzylcarbamate (12)

A 160 cc stainless steel Parr autoclave Was charged with 5.19 g (0.03 mol) 4-aminomethyl-1,8-octanediamine (TAN), 17.9 g (0.096 mol) N-cyclohexyl-N',N',N'',N'''-tetramethylguanidine, and 30.mL 1-methyl-2-pyrrolidinone (N-MP). The autoclave was attached to a pressure head and at room temperature with stirring was added 160 psig carbon dioxide. Addition of CO₂ resulted in an exothermic reaction with a rise in temperature to ca. 40° C. Into a Fischer-Porter bottle was added 22.8 g (0.18 mol) benzyl chloride. This was attached to a pressure head and 80 psig carbon dioxide was added above the solution. After 1 h the benzyl chloride solution was added all at once under 80 psig CO₂ to the pre-formed carbamate anion solution generated in the first Fischer-Porter bottle. After addition the pressure was raised again to 160 psig with carbon dioxide and the reaction mixture was warmed to 55° C. for 18 h. After this time the reaction mixture was allowed to cool to room temperature and then the pressure was released. The crude material was poured into 100 mL ethyl acetate and extracted with 2×100 mL 0.5 M aq. HCl followed by 100 mL brine. The organic layer was dried over Na₂CO₃, filtered and concentrated. After crystallization from ethyl acetate/hexane an isolated yield of 58% (9.01 g) of the tricarbamate 12 resulted. m.p. 78–80° C. ¹H NMR (CDCl₃) δ 7.4–7.34 (m, 5H), 5.1 (s, 6H), 5.1–5.0 (br, N—H, 3H), 3.2–3.05 (m, 6H), 1.6–1.2 (overlapping m, 11H). ¹³C{¹H} NMR (CDCl₃) δ 157.4, 157.1, 137.2, 129.0, 1286, 67.2, 67.1, 44.0, 41.6, 38.6, 31.4, 30.7, 28.9, 27.3, 23.9. IR (CHCl₃) 3453, 1713. Anal. Calcd.: C, 68.85; H, 7.18; N, 7.30. Found: C, 69.39; H, 7.32; N, 7.32.

EXAMPLE 15

Hexamethylene-1,6-bis(benzylcarbamate) (13)

A 160 cc stainless steel Parr autoclave was charged with 4.64 g (0.04 mol) 1,6-diaminohexane, 16.75 g (0.085 mol) N-cyclohexyl-N',N',N'',N'''-tetramethylguanidine, and 30 mL 1-methyl-2-pyrrolidinone (N-MP). The autoclave was attached to a pressure head and at room temperature with stirring was added 160 psig carbon dioxide. Addition of CO₂ resulted in an exothermic reaction with a rise in temperature to ca. 40° C. Into a Fischer-Porter bottle was added 20 g (0.158 mol) benzyl chloride. This was attached to a pressure head and 80 psig carbon dioxide was added above the solution. After 1 h the benzyl chloride solution was added all at once under 80 psig CO₂ to the pre-formed carbamate anion solution generated in the first Fischer-Porter bottle. After addition the pressure was raised again to 160 psig with carbon dioxide and the reaction mixture was warmed to 55° C. for 18 h. After this time the reaction mixture was allowed to cool to room temperature and then the pressure was released. The crude material was poured into 200 mL H₂O and a white precipitate formed. This white material was collected by filtration and was washed with water followed by air drying at room temperature overnight giving 9.75 g (63.5%) of the dicarbamate 13. m.p. 130–132° C. ¹H NMR (CDCl₃) δ 7.4–7.3 (overlapping m, 10H), 5.13 (S, 4H), 4.85 (br, N—H, 2H), 3.21 (q, J=6.3 Hz, 4H), 1.52 (br m, 4H), 1.36 (br, 4H). ¹³C{¹H} NMR (CDCl₃) δ 157.0, 137.2, 129.0, 128.6 (overlapping), 67.1, 41.4, 30.4, 26.7. IR (CHCl$_3$) 3453, 1713; MS (FAB) m/z=385 (MH+) Anal Calcd.: C, 68.73; H, 7.34; N, 7.29. Found: C, 68.70; H, 7.40; N, 7.19.

TABLE 3

RR'NH + CO$_2$ + CyTMG $\xrightarrow[\text{Benzyl—Cl}]{\text{Solvent}}$ RR'NCO$_2$CH$_2$Ph + RR'NCH$_2$Ph

| Example # | RR'NH | Temp °C. | Solvent | % Urethane G.C. Yield (Compound #) | Isolated Yield | % Amine[1] G.C. Yield |
|---|---|---|---|---|---|---|
| 3 | Bu$_2$NH | 40 | CH$_3$CN | 95(1) | 64 | <1 |
| 4 | Et$_2$NH | 40 | CH$_3$CN | 95(2) | 47 | <1 |
| 5 | BuNH$_2$ | 55 | CH$_3$CN | 95(3) | 64 | 9 |
| 6 | s-BuNH$_2$ | 55 | CH$_3$CN | 89(4) | 44 | <1 |
| 7 | t-BuNH$_2$ | 55 | CH$_3$CN | 90(5) | 41 | <1 |
| 8 | c-C$_8$H$_{17}$NH$_2$ | 55 | CH$_3$CN | 99.5(6) | 53 | <1 |
| 9 | CyNH$_2$ | 55 | CH$_3$CN | 97(7) | 50 | <1 |
| 10 | CyCH$_2$NH$_2$ | 55 | CH$_3$CN | 105(8) | 76 | <1 |
| 11 | PhNH$_2$ | 55 | CH$_3$CN | 90(9) | 64 | <1 |
| 12 | (NH$_2$CH$_2$CH$_2$)$_2$NH | 55 | CH$_3$CN | —(10) | 50 | — |
| 13 | 1,4-(NH$_2$Cy)$_2$CH$_2$ | 55 | NMP[3] | —(11) | 78 | — |
| 14 | Triaminononane[2] | 55 | NMP[3] | —(12) | 58 | — |
| 15 | H$_2$N(CH$_2$)$_6$NH$_2$ | 55 | NMP[3] | —(13) | 63.5 | — |

All reactions were run under 80 psig carbon dioxide pressure and run to completion. limiting reagent is the amine. An excess of benzyl chloride as used in all reactions and G.C. yields are based on biphenyl internal standard.
[1]% Amine indicated by G.C. is the approximate amount of products derived from nitrogen attack on benzyl chloride.
[2]Triaminononane = 4-aminomethyl-1,8-octanediamine.
[3]NMP = 1-methyl-2-pyrrolidinone.

EXAMPLE 16

Cbz-dibenxylaspartate (14)

A Fischer Porter bottle was charged with 2.66 g (0.02 mol) L-aspartic acid, 12.77 g (0.084 mol) 1,8-diazabicyclo[5.4.0]undec-7-ene and 25 mL CH$_3$CN. The Fischer-Porter bottle was attached to a pressure head and at room temperature with stirring was added 80 psig carbon dioxide. Addition of CO$_2$ resulted in an exothermic reaction with a rise in temperature to ca. 40° C. Into a second Fischer-Porter bottle was added 15 g (0.12 mol) benzyl chloride in 10 mL CH$_3$CN. This mixture was attached to a pressure head and 80 psig carbon dioxide was added above the solution. After 1 h the benzyl chloride solution was added all at once under 80 psig CO$_2$ to the pre-formed carbamate anion solution generated in the first Fischer-Porter bottle. After addition the reaction mixture was warmed to 55° C. for 3 h. After this time the reaction mixture was allowed to cool to room temperature and then the pressure was released. The crude material was poured into 100 mL diethyl ether and extracted with 2×100 mL 0.5 M aq. HCl followed by 100 mL brine. The organic layer was dried over MgSO$_4$, filtered and concentrated. The excess benzyl chloride was removed by adding hexane to the crude residue leaving a light yellow oil. Crystallization form diethyl ether/hexane gave 5.34 g (60%) of Cbz-dibenzyl aspartate 14. Product identified by NMR spectroscopy and was identical to authentic material. $[\alpha]_D^{23} = -1.8$ (authentic material $= -1.9$).

EXAMPLE 17

1,6-Hexamethylene-bis-(p-vinylbenzylcarbamate) (15)

A Fischer Porter bottle was charged with 4 g (0.035 mol) 1,6-diaminohexane, 14 g (0.092 mol) 1,8-diazabicyclo[5.4.0]undec-7-ene and 30 mL CH$_3$CN. The Fischer-Porter bottle was attached to a pressure head and at room temperature with stirring was added 80 psig carbon dioxide. Addition of CO$_2$ resulted in an exothermic reaction with a rise in temperature to ca. 40° C. Into a second Fischer-Porter bottle was added 20 g (0.13 mol) p-vinylbenzyl chloride. This was attached to a pressure head and 80 psig carbon dioxide was added above the solution. After 1 h the benzyl chloride solution was added all at once under 80 psig CO$_2$ to the pre-formed carbamate anion solution generated in the first Fischer-Porter bottle. After addition the reaction mixture was warmed to 55° C. for 4 h. After this time the reaction mixture was allowed to cool to room temperature and then the pressure was released. The crude material was poured into 200 mL 0.5 M aq. HCl giving a white solid. This solid was collected by filtration and was washed with water followed by air drying at room temperature giving 6.8 g (45%) of the dicarbamate 15. m.p. (decomposition > 153° C.). $^1$H NMR (CDCl$_3$) δ 7.43 (d, J=8.3 Hz, 4H), 7.34 (d, J=8.1 Hz, 4H), 6.74 (dd, J=17.7, 10.8 Hz, 2H), 5.78 (dd, J=17.6, 0.9 Hz, 2H), 5.29 (dd, J=10.8, 0.9 Hz, 2H), 5.11 (s, 4H), 4.8 (br, N—H, 2H), 3.20 (br, 4H), 1.50 (br, 4H), 1.35 (br, 2H). $^{13}$C{$^1$H} NMR (CDCl$_3$) δ 156.9, 138.0, 136.9, 136.7, 128.9, 126.9, 114.7, 66.9, 41.4, 30.4, 26.7. IR (CHCl$_3$) 3452, 1709. Anal. Calcd.: C, 71.53; H, 7.39; N, 6.42. Found: C, 71.72; H, 7.45; N, 6.48.

EXAMPLE 18

α,α'-Bis-(N,N-diethyl)-p-xylylcarbamate (16)

A Fischer Porter bottle was charged with 1.46 g (0.02 mol) diethyl amine, 3.43 g (0.022 mol) 1,8-diazabicyclo[5.4.0]undec-7-ene and 20 mL N,N-dimethylformamide. The Fischer-Porter bottle was attached to a pressure head an-d at room temperature with stirring was added 80 psig carbon dioxide. Addition of CO$_2$ resulted in an exothermic reaction with a rise in temperature to ca. 40° C. Into a second Fischer-Porter bottle was added 0.88 g (0.005 mol) α,α'-dichloro-p-xylene in 15 ml DMF. This was attached to a pressure head and 80 psig carbon dioxide was added above the solution. After 1 h the di-chloride solution was added all at once under 80 psig CO$_2$ to the pre-formed carbamate anion solution generated in the first Fischer-Porter bottle. After addition the reaction mixture was warmed to 40° C. for 21 h. After this time the reaction mixture was allowed to cool to room temperature and then the pressure was released. The crude material was poured into 100 mL diethyl ether and was then extracted with 2×100 mL 0.5 M aq. HCl and 100 mL brine. The ethereal layer was dried over $Na_2CO_3$, filtered and concentrated. The residue was chromatographed on silica gel using 25% ethyl acetate/hexane giving 0.96 g (66%) of the dicarbamate 16. m.p. 61-63 C. $^1H$ NMR (CDCl$_3$) $\delta$ 7.36 (s, 4H), 5.14 (s, 4H), 3.31 (q, J=6.9 Hz, 8H), 1.14 (t, J=7.2 Hz, 12 H). $^{13}C\{^1H\}$ NMR (CDCl$_3$) $\delta$ 156.3, 137.3, 128.3, 66.9, 42 (br), 14.5 (br). IR (CHC13) 1692; MS (thermal spray) m/z=337 (MH+). Anal. Calcd.; C, 64.26; H, 8.39; N, 8.33. Found: C, 64.73; H, 8.60; N, 8.36.

The following Examples 19-30 illustrate the present process utilizing various amines, polar aprotic solvents, hydrocarbyl halides and reaction temperatures. A summary of these examples is set forth in Table 4.

EXAMPLE 19

N,N-dibutyl butylcarbamate (17)

A Fischer-Porter bottle was charged with 2.58 g (0.02 mol) N,N-dibutyl amine, 5.32 g (0.027 mol) N-cyclohexyl-N',N',N'',N''-tetramethylguanidine, 154 mg biphenyl as internal G.C. standard and 20 mL CH$_3$CN. The Fischer-Porter bottle was attached to a pressure head and at room temperature with stirring was added 80 psig carbon dioxide. Addition of CO$_2$ resulted in an exothermic reaction with a rise in temperature to ca. 40° C. Into a second Fischer-Porter bottle was added 7.4 g (0.08 mol) butyl chloride in 10 mL CH$_3$CN. This was attached to a pressure head and 80 psig carbon dioxide was added above the solution. After 1 h the benzyl chloride solution was added all at once under 80 psig CO$_2$ to the pre-formed carbamate anion solution generated in the first Fischer-Porter bottle. After addition the reaction mixture was warmed to 70° C. for 17.5 h. After this time the reaction mixture was allowed to cool to room temperature and then the pressure was released. An aliquot was taken, diluted with ether, solid Cl$^-$+HCyTMG filtered off and analyzed by G.C. (93.5% yield calculated). Oil. $^1H$ NMR (CDCl$_3$) $\delta$ 4.08 (t, J=6.6 Hz, 2H), 3.21 (br, 4H), 1.65-1.3 (overlapping m, 12H), 0.95 (t, J=7.3 Hz, 3H), 0.94 (t, J=7.3 Hz, 6H). $^{13}C\{^1H\}$ NMR (CDCl$_3$) $\delta$ 157.1, 65.3, 47.4 (br), 31.7, 31.2 (br), 20.5, 19.7, 14.4, 14.2. IR (film) 1703; MS m/z=230 (MH+). Anal. Calcd.: C, 68.08; H, 11.87; N, 6.11. Found: C, 68.32; H, 10.92; N, 6.06.

EXAMPLE 20

N,N-diethyl butylcarbamate (18)

A 160 cc stainless steel Parr autoclave was charged with 2.19 g (0.03 mol) diethyl amine, 8.46 g (0.043 mol) N-cyclohexyl-N',N',N'',N''-tetramethylguanidine, 310 mg (0.002 mol) biphenyl as internal G.C. standard, and 25 mL CH$_3$CN. The autoclave was attached to a pressure head and at room temperature with stirring was added 160 psig carbon dioxide. Addition of CO$_2$ resulted in an exothermic reaction with a rise in temperature to ca. 40° C. Into a Fischer-Porter bottle was added 8.325 g (0.09 mol) butyl chloride in 10 mL CH$_3$CN. This mixture was attached to a pressure head and 80 psig carbon dioxide was added above the solution. After 1 h the butyl chloride solution was added all at once under 80 psig CO$_2$ to the pre-formed carbamate anion solution generated in the autoclave. After addition the pressure was raised to 160 psig with carbon dioxide and the reaction mixture was warmed to 70° C. for 1.5 h. After this time the reaction mixture was allowed to cool to room temperature and then the pressure was released. An aliquot was taken, diluted with diethyl ether, Cl$^-$+HCyTMG precipitated from solution and was filtered off, and by G.C. analysis a 97% yield of urethane was calculated. The crude material was poured into 100 mL ethyl acetate and extracted with 2×100 mL 0.5 M aq. HCl followed by 100 mL brine. The organic layer was dried over $Na_2CO_3$, filtered and concentrated leaving a light yellow residue. This was distilled and N,N-diethyl butylcarbamate was collected at 70-71° C. (ca. 3 torr), 3.16 g (61%). Oil. $^1H$ NMR (CDCl$_3$) $\delta$ 4.06 (t, J=6.5 Hz, 2H), 3.26 (q, J=7.1 Hz, 4H), 1.61(m, 2H), 1.37 (m, 2H), 1.10 (t, J=7.2 Hz, 6H), 0.93 (t, J=7.3 Hz, 3H). $^{13}C\{^1H\}$ NMR (CDCl$_3$) $\delta$ 156.6, 65.3, 41.9, 31.7, 19.7, 14.2. IR (film) 1700; MS (thermal spray) m/z=174 (MH+). Anal. Calcd.: C, 62.39; H, 11.05; N, 8.08. Found: C, 61.84; H, 10.61; N, 7.97.

EXAMPLE 21

N-butyl butylcarbamate (19)

Procedures as described in synthesis of 18, using 1,8-diazabicyclo[5.4.0]undec-7-ene in place of CyTMG. A G.C. yield of 82% was calculated and a 71% isolated yield of N-butyl butylcarbamate resulted after chromatography on silica gel. Oil. $^1H$ NMR (CDCl$_3$) $\delta$ 4.75 (br, N—H), 4.05 (t, J =6.7 Hz, 2H), 3.15 (t, J=6.9HZ, 2H), 1.61-1.32 (overlapping m, 8H), 0.92 (t, J=7.31 Hz, 3H), 0.91 (t, J=7.2 Hz, 3H). $^{13}C\{^1H\}$ NMR (CDCl$_3$) $\delta$ 157.4, 65.1, 41.3, 32.6, 31.6, 20.4, 19.6, 14.2 (overlapping). IR (film) 3337, 1700; MS (thermal spray) m/z=174 (MH+).

EXAMPLE 22

N-phenyl butylcarbamate (20)

Procedures as described in synthesis of 18, using 1,8-diazabicyclo[5.4.0]undec-7-ene in place of CyTMG. A G.C. yield of 67% was calculated and a 58% isolated yield of N-phenyl butylcarbamate resulted after chromatography on silica gel. m.p. 63.5-65° C. $^1H$ NMR (CDCl$_3$) $\delta$ 7.44 (d, J=8 Hz, 2H), 7.34·(t, J=8 Hz, 2H), 7.09 (t, J=7.3 Hz, 1H), 6.83 (br, N—H), 4.22 (t, J=6.7 Hz, 2H), 1.70 (m, 2H), 1.45 (m, 2H), 1.00 (t, J=7.3 Hz, 3H). $^{13}C\{^1H\}$ NMR (CDCl$_3$) $\delta$ 154.4, 138.6, 129.5, 123.8, 119.2, 65.6, 31.5, 19.6, 14.3. IR (CHCl$_3$) 3438, 1730; MS (FAH) m/z=194 (MH+). Anal. Calcd : C, 68.37; H, 7.82; N, 7.25. Found: C, 68.57; H, 7.95; N, 7.29.

EXAMPLE 23

4,4'-methylene-bis(cyclohexyl)-bis-(butylcarbamate) (21)

A 160 cc stainless steel Parr autoclave was charged with 3.15 g (0.03 mol) 4,4'-methylenebis(cyclohexylamine), 6.9 g (0.035 mol) N-cyclohexyl-N',N',N'',N''-tetramethylguanidine and 35 mL CH$_3$CN. The autoclave was attached to a pressure head and at room temperature with stirring was added 160 psig carbon dioxide. Addition of CO$_2$ resulted in an exothermic reaction with a rise in temperature to ca. 40° C. Into a Fischer-Porter bottle was added 8.33 g (0.09 mol) butyl chloride in 10 mL CH$_3$CN. This mixture was attached to a pressure head and 80 psig carbon dioxide was added above the solution. After 1 h the butyl chloride solution was added all at once under 80 psig CO$_2$ to the pre-formed carbamate anion solution generated in the autoclave. After addition the pressure was raised to 160 psig with carbon dioxide and the reaction mixture was warmed to 85° C. for 6 h. After this time the reaction mixture was allowed to cool to room temperature and then the pressure was released. The crude material was poured into 100 mL ethyl acetate and extracted with 2×100 mL 0.5 M aq. HCl followed by 100 mL brine. The organic layer was dried over $Na_2CO_3$, filtered and concentrated leaving a light yellow residue. This was passed through a short column of silica gel using $CH_2Cl_2$ as an eluent giving 5.48 g (89%) of the dibutyl carbamate 21. IR ($CHCl_3$) 3449, 1705; MS m/z=411 (MH+). Anal. Calcd.: C, 67.28; H, 10.31; N, 6.82. Found: C, 67.27; H, 10.09; N, 6.84.

EXAMPLE 24

TAN-Tributylcarbamate (22)

A 300 cc stainless steel Parr autoclave was added 17.3 g (0.1 mol) 4-aminomethyl-1,8-octanediamine, 60 g (0.305 mol) N-cyclohexyl-N',N',N'',N''-tetramethylguanidine and 75 mL 1-methyl-2-pyrrolidinone (N-MP). The autoclave was attached to a pressure head and at room temperature with stirring was added 160 psig carbon dioxide. Addition of $CO_2$ resulted in an exothermic reaction with a rise in temperature to ca. 40° C. Into a Fischer-Porter bottle was added 55.5 g (0.6 mol) butyl chloride. This mixture was attached to a pressure head and 80 psig carbon dioxide was added above the solution. After 1 h the butyl chloride solution was added all at once under 80 psig $CO_2$ to the pre-formed carbamate anion solution generated in the autoclave. After addition the pressure was raised to 160 psig with carbon dioxide and the reaction mixture was warmed to 85° C. for 18h. After this time the reaction mixture was allowed to cool to room temperature and then the pressure was released. The crude material was poured into 200 mL ethyl acetate and extracted with 2×200 mL 0.5 M aq. HCl followed by 200 mL brine. The organic layer was dried over $Na_2CO_3$, filtered and concentrated leaving a light yellow residue. This was crystallized from ethyl acetate/hexane giving 36.5 g (85.5%) of the tributyl carbamate 22. m.p. 60–61° C. $^1H$ NMR ($CDCl_3$) δ 4.85 (br, N—H, 3H) 4.05 (t J=6.6 Hz 6H), 3.2–3.05 (m, 6H), 1.65-1.2 (overlapping m, 23H), 0.93 (t, J=7.3 Hz, 9H). $^{13}C\{^1H\}$ NMR ($CDCl_3$) δ 157.7, 157.5, 65.2, 65.1, 44.0, 41.5, 40.9, 38.6, 31.6, 31.5, 30.8, 28.9, 27.4, 24.0, 19.6, 14.2. IR ($CHCl_3$) 3455, 1709. Anal. Calcd.: C, 60.86; H, 10.0; N, 8.87. Found: C, 60.79; H, 10.38; N, 8.87.

EXAMPLE 25

N-phenyl-2-propylcarbamate (23)

Procedures as described in synthesis of 18, using 1,8-diazabicyclo[5.4.0]undec-7-ene in place of CyTMG and 2-chloropropane in place of butyl chloride. A G.C. yield of 54% was calculated and a 20.5% isolated yield of N-phenyl butylcarbamate resulted after chromatography on silica gel. (A small amount of diphenyl urea was detected by G.C. in this particular reaction.) m.p. 88–89 ° C. (literature m.p. 90° C.) $^1H$ NMR ($CD_2Cl_2$) δ 7.46 (d, J=8.7 Hz, 2H), 7.35 (t, J=8.0 Hz, 2H), 7.10 (t, J=7.5 Hz, 1H), 6.9 (br, N—H), 5.06 (7 lines, J=6.3 Hz, 1H), 1.34 (d, J=6.3 Hz, 6H). $^{13}C\{^1H\}$ NMR ($CD_2Cl_2$) δ 154.2, 139.4, 129.8, 124.0, 119.5, 69.5, 22.8. IR ($CHCl_3$) 3437, 1728; MS (thermal spray) m/z=180 (MH+). Anal. Calcd.: C, 67.02; H, 7.31; N, 7.82. Found: C, 67.35; H, 7.45; N, 7.85.

EXAMPLE 26

4,4'-methylene-bis(cyclohexyl)-bis-(2-methoxyethyloarbamate) (24)

Procedures as described in synthesis of 21, using 2-chloroethyl methyl ether in place of butyl chloride. A 70% isolated yield of the dicarbamate 24 resulted after chromatography on silica gel. IR ($CHCl_3$) 3441, 1715; MS m/z=415 (MH+). Anal. Calcd.: C, 60.85; H, 9.24; N, 6.76. Found: C, 60.68; H, 9.59; N, 6.80.

EXAMPLE 27

N-Cyclohexyl allylcarbamate (25)

A Fischer Porter bottle was charged with 1.98 g (0.02 mol) cyclohexyl amine, 5.30 g (0.027 mol) N-cyclohexyl-N',N',N'',N''-tetramethylguanidine, 154 mg (0.001 mol) biphenyl as internal G.C. standard, and 20 mL $CH_3CN$. The Fischer-Porter bottle was attached to a pressure head and at room temperature with stirring was added 80 psig carbon dioxide. Addition of $CO_2$ resulted in an exothermic reaction with a rise in temperature to ca. 40° C. Into a second Fischer-Porter bottle was added 4.6 g (0.06 mol) allyl chloride in 10 mL $CH_3CN$. This mixture was attached to a pressure head and 80 psig carbon dioxide was added above the solution. After 1 h the allyl chloride solution was added all at once under 80 psig $CO_2$ to the pre-formed carbamate anion solution generated in the first Fischer-Porter bottle. After addition the reaction mixture was warmed to 55° C. for 5 h. After this time the reaction mixture was allowed to cool to room temperature and then the pressure was released. An aliquot was taken, diluted with diethyl ether, Cl−+HCyTMG precipitated from solution and was filtered off, and by G.C. analysis a 97% yield of N-cyclohexyl allylcarbamate, 25, was calculated.

EXAMPLE 28

Piperazino-bis(allylcarbamate) (26)

A Fischer Porter bottle was charged with 12.9 g (0.15 mol) piperazine, 62 g (0.41 mol) 1,8-diazabicycl[5.4.-0]undec-7-ene and 90 mL N,N-dimethylformamide. The Fischer-Porter bottle was attached to a pressure head and at room temperature with stirring was added 60 psig carbon dioxide. Addition of $CO_2$ resulted in an exothermic reaction and cooling with ice was required. Into a second Fischer-Porter bottle was added 55 g (0.72 mol) allyl chloride in 15 mL DMF. This mixture was attached to a pressure head and 60 psig carbon dioxide was added above the solution. After 1h the allyl chloride solution was added all at once under 60 psig $CO_2$ to the pre-formed carbamate anion solution generated in the first Fischer-Porter bottle. After addition the reaction mixture was warmed to 50° C. for 3h. After this time the reaction mixture was allowed to cool to room temperature and then the pressure was released. The crude material was poured into 300 mL 0.5 M aqueous HCl. A heavy oil settled to the bottom. This oil was collected, dissolved in 100 mL diethyl ether, dried over $Na_2CO_3$ filtered and concentrated. Addition of hexane followed by cooling in the freezer gave 32.8 g (86%) of the dicarbamate 26 m.p. 54–55 ° C. $^1H$ NMR ($CDCl_3$) δ 5.94 (m, 2H), 5.31 (dq, J=17.2, 1.5 Hz, 2H), 5.23 (dq, J=10.3, 1 3 Hz, 2H), 4.61 (dt, 5.6, 1.3 Hz, 4H), 3.5 (s, 8H). $^{13}C\{^1H\}$ NMR (CDC13) δ 155.5, 133.3, 118.2, 66.8, 44.1. IR ($CHCl^3$) 1690, 1649; MS (EI)

m/z=254 (MH+). Anal. Calcd.: C, 56.68; H, 7.13; N, 11.02. Found: C, 56.73; H, 7.26; N, 11.03.

EXAMPLE 29

4,4'methylene-bix(cyclohexyl)-bis-(allylcarbamate) (27)

A Fischer Porter bottle was charged with 2.1 g (0.01 mol) 4,4'-methylene-bis(cyclohexylamine), 5.3 g (0.027 mol) N-cyclohexyl-N',N',N'',N''-tetramethylguanidine and 20 mL 1-methyl-2-pyrrolidinone. The Fischer-Porter bottle was attached to a pressure head and at room temperature with stirring was added 80 psig carbon dioxide. Addition of $CO_2$ resulted in an exothermic reaction and cooling with ice was required. Into a second Fischer-Porter bottle was added 4.6 g (0.06 mol) allyl chloride in 10 mL N-MP. This mixture was attached to a pressure head and 80 psig carbon dioxide was added above the solution. After 1 h the allyl chloride solution was added all at once under 80 psig $CO_2$ to the pre-formed carbamate anion solution generated in the first Fischer-Porter bottle. After addition the reaction mixture was warmed to 55° C. for 20 h. After this time the reaction mixture was allowed to cool to room temperature and then the pressure was released. The crude material was poured into 200 mL ethyl acetate and extracted with 2×200 mL 0.5 M aq. HCl followed by 200 mL brine. The organic layer was dried over $Na_2CO_3$, filtered and concentrated leaving a light yellow solid. This was dissolved in methylene chloride and passed through a short column of silica gel using ethyl acetate/$CH_2Cl_2$ as eluent. Concentration of the filtrate gave 2.89 g (76.5%) of the dicarbamate 27. IR ($CHCl_3$) 3441, 1713; MS (EI) m/z=379 (MH+). Anal. Calcd.: C, 66.64; H, 9.05; N, 7.40. Found: C, 66.67; H, 9.32; N, 7.36.

EXAMPLE 30

Hexamethylene-bis-1,6-(allycarbamate) (28)

A 160 cc Parr autoclave was charged with 4.4 g (0.038 mol) 1,6-diaminohexane, 15.4 g (0.10 mol) 1,8-diazabicycl[5.4.0]undec-7-ene, 403 mg tridecane as internal G.C. standard and 30 mL N,N-dimethylformamide. The autoclave was attached to a pressure head and at room temperature with stirring was added 160 psig carbon dioxide. Addition of $CO_2$ resulted in an exothermic reaction with a rise in temperature to ca. 40° C. Into a Fischer-Porter bottle was added 12 g (0.157 mol) allyl chloride in 20 mL DMF. This mixture was attached to a pressure head and 80 psig carbon dioxide was added above the solution. After 1 h the allyl chloride solution was added all at once under 80 psig $CO_2$ to the pre-formed carbamate anion solution generated in the autoclave. After addition the pressure was raised to 160 psig with carbon dioxide and the reaction mixture was warmed to 65° C. for 17.5 h. After this time the reaction mixture was allowed to cool to room temperature and then the pressure was released. An aliquot was taken, diluted with diethyl ether, Cl−+HDBU filtered off, and by G.C. a 40% yield of dicarbamate was calculated. The reaction mixture was poured into 150 mL water giving a white solid. This solid was collected by filtration, washed with water and crystallized from $CH_2Cl_2$/hexane giving 3.52 g (33%) of the dicarbamate 28. m.p. 72.5–74° C. $^1H$ NMR ($CDCl_3$) δ 5.92 (m, 2H), 5.31 (dq, J=17.2, 1.6 Hz, 2H), 5.21 (dq, J=10.4, 1.3 Hz, 2H), 4.89 (br, N—H, 2H), 4.56 (d, J=5.5 Hz, 4H),3.20 (q, J=6.6 Hz, 4H), 1.51 (m, 4H), 1.35 (m, 4H). $^{13}C\{^1H\}$ NMR ($CDCl_3$) δ 156.9, 133.5, 118.0, 41.3, 30.4, 26.7. IR ($CHCl_3$) 3453, 1713, 1649; MS (EI) m/z=285 (MH.). Anal. Calcd.: C, 59.14; H, 8.51; N, 9.85. Found: C, 59.30; H, 8.73; N, 9.70.

TABLE 4

$$RR'NH + CO_2 + Base \xrightarrow[R''Cl]{Solvent} RR'NCO_2R''$$

| Rxn # | RR'NH | R''Cl | Base[2] | Temp (°C.) | Solvent[3] | % Urethane G.C. Yield (Compound #) | Isolated Yield |
|---|---|---|---|---|---|---|---|
| 19 | $Bu_2NH$ | Bu—Cl | CyTMG | 70 | $CH_3CN$ | 93.5(17) | — |
| 20 | $Et_2NH$ | Bu—Cl | CyTMG | 70 | $CH_3CN$ | 97(18) | 61 |
| 21 | $BuNH_2$ | Bu—Cl | DBU | 85 | $CH_3CN$ | 82(19) | 71 |
| 21 | $BuNH_2$ | Bu—Cl | CyTMG | 85 | $CH_3CN$ | 73(19) | — |
| 22 | $PhNH_2$ | Bu—Cl | DBU | 85 | $CH_3CN$ | 67(20) | 58 |
| 23 | $1,4(NH_2Cy)_2CH_2$ | Bu—Cl | DBU | 85 | $CH_3CN$ | —(21) | 90 |
| 23 | $1,4(NH_2Cy)_2CH_2$ | Bu—Cl | CyTMG | 85 | $CH_3CN$ | —(21) | 89 |
| 24 | Triaminononane[1] | Bu—Cl | CyTMG | 85 | N—MP | —(22) | 85.5 |
| 25 | $PhNH_2$ | i-Pr—Cl | DBU | 90 | $CH_3CN$ | 54(23) | 20.5 |
| 26 | $1,4(NH_2Cy)_2CH_2$ | $MeOCH_2CH_2Cl$ | CyTMG | 85 | $CH_3CN$ | —(24) | 70 |
| 27 | $CyNH_2$ | $CH_2=CHCH_2Cl$ | CyTMG | 55 | $CH_3CN$ | 97(25) | — |
| 28 | $HN(CH_2CH_2)_2NH$ | $CH_2=CHCH_2Cl$ | DBU | 50 | DMF | —(26) | 86 |
| 29 | $1,4(NH_2Cy)_2CH_2$ | $CH_2=CHCH_2Cl$ | CyTMG | 55 | N—MP | —(27) | 76.5 |
| 30 | $H_2N(CH_2)_6NH_2$ | $CH_2=CHCH_2Cl$ | DBU | 65 | DMF | 40(28) | 33 |

All reactions run under 80–160 psig carbon dioxide pressure and carried to completion (limiting reagent = amine in all cases).
G.C. Yields based on biphenyl as internal standard.
[1]Triaminononane = 4-aminomethyl-1,8-octanediamine.
[2]CyTMG = N-cyclohexyl-N',N',N'',N''-tetramethylguanidine. DBU = 1,8-diazabicyclo[5.4.0]undec-7-end.
[3]N—MP = 1-methyl-2-pyrrolidinone. DMF = N,N-dimethylformamide.

EXAMPLE 3

Butyl-1,4-bix(N,N-dibutylcarbamate) (29)

A 300 cc stainless steel Parr autoclave charge with 32.25 g (0.25 mol) N,N-dibutyl amine, 50.2 g (0.255 mol) N-cyclohexyl-N',N',N'',N''-tetramethylguanidine and 75 mL $CH_3CN$. The autoclave was attached to a pressure head and at room temperature with stirring was added 160 psig carbon dioxide. Addition of $CO_2$ resulted in an exothermic reaction with a rise in temperature to ca. 40° C. Into a Fischer-Porter bottle was added 9.53 g (0.075 mol) 1,4-dichlorobutane in 10 mL $CH_3CN$. This mixture was attached to a pressure head and 80 psig carbon dioxide was added above the solution. After 1h the dichlorobutane solution was added all at once under 80 psig $CO_2$ to the pre-formed carbamate anion solution generated in the autoclave. After addition the pressure was raised to 160 psig with carbon dioxide and the reaction mixture was warmed to 75° C. for 16h.

After this time the reaction mixture was allowed to cool to room temperature and then the pressure was released. The crude material was poured into 200 mL ethyl acetate and extracted with 2×200 mL 0.5 M aq. HCl followed by 200 mL brine. The organic layer was dried over $Na_2CO_3$, filtered and concentrated leaving a light yellow residue. This was chromatographed on silica gel using ethyl acetate/hexane giving 21 g (70%) of the dicarbamate 29. Oil. $^1$H NMR ($CDCl_3$) δ 4.1 (m, 4H), 3.2 (br m, 8H), 1.7 (m, 4H), 1.51 (m, 8H), 1.30 (sextet, J=7.4 Hz, 8H), 0.92 (t, J=7.3 Hz, 12H). $^{13}$C{$^1$H} NMR δ 156.8, 65.1, (47.6, 47.1), (31.3, 30.8), 26.4, 20.5, 14.3. IR (film) 1701; MS (FAB) m/z=401 (MH+). Anal. Calcd.: C, 65.96; H, 11.07; N, 6.99. Found: C, 66.22; H, 11.12; N, 7.40.

EXAMPLE 32

Butyl-1,4-bis(N,N-diethylcarbamate) (30)

Procedures as described in synthesis of 29, using 1,8-diazabicyclo[5.4.0] undec-7-ene in place of N-cyclohexyl-N', N", N"'-tetramethylguanidine and N,N-dimethylformamide in place of $CH_3CN$. A G.C. yield of 96.5% was calculated using biphenyl as internal standard. Oil $^1$H NMR ($CDCl_3$) δ 4.1 (m, 4H), 3.26 (q, J=7 Hz, 8H), 1.72 (m, 4H), 1.11 (t, J=7.1 Hz, 12H). $^{13}$C{$^1$H} NMR ($CDCl_3$) 67 156.4, 65.1, 41.9, 26.4, 14.3. IR (film) 1696 (literature=1689); MS m/z=(MH+). Anal. Calcd.: C, 58.31; H, 9.79; N, 9.71. Found: C, 58.30; H, 9.64; N, 9.72.

EXAMPLE 33

Butyl-1,4-bis(N,N-diallylcarbamate) (31)

Procedures as described in synthesis of 29, using 1,8-diazabicyclo[5.4.0]undec-7-ene in place of N-cyclohexyl-N',N",N"'-tetramethylguanidine. Isolation by passage of the crude reaction material through silica gel using dicarbamate 31. Oil $^1$H NMR ($CDCl_3$) δ 5.78 (m, 4H), 5.17 (overlapping br m, 8H), 4.14 (m, 4H), 3.87 (br, 8H), 1 73 (m, 4H). 13C (1H} NMR ($CDCl_3$) δ 156.7, 134.1, 117.0 (br), 65.5, 49.3 (br), 26.3. IR (film) 1700, 1644; MS (thermal spray) m/z=337 (MH+). Anal. Calcd.: C, 64.26; H, 8.39; N, 8.33. Found: C, 64.12; H, 8.62; N, 8.32.

EXAMPLE 34

Butyl-1,4-bis(N-butylcarbamate) (32)

Procedures as described in synthesis of 29. A G.C. yield of 91.5% Was calculated using biphenyl as internal standard. Product isolated by pouring crude reaction material into water and collecting the white solid by filtration. After washing with water and air drying a 77% isolated yield of the dicarbamate 32 resulted. m.p. 114-115° C. $^1$H NMR ($CDCl_3$) δ 4.7 (br, N—H, 2H), 4.09 (br, 4H), 3.17 (br q, J=6 Hz, 4H), 1.69 (br, 4H), 1.52-1.31 (overlapping m, 8H), 0.93 (t, J=7.2 Hz, 6H). $^{13}$C {$^1$H} NMR ($CDCl_3$) δ 157.2, 64.8, 41.2, 32.6, 26.2, 20.4, 14.2. IR ($CHCl_3$) 3453, 1711; MS (thermal spray) m/z=289 (MH+). Anal. Calcd.: C, 58.31; H, 9.79; N, 9.71. Found: C, 58.71; H, 10.05; N, 9.80.

EXAMPLE 35

Ethyl-1,2-bis(N,N-diethylcarbamate) (33)

Procedures as described in synthesis of 29. A G.C. yield of 85% was calculated using biphenyl as internal standard and an isolated yield of 45% of the dicarbamate 33 resulted. Oil $^1$H NMR ($CDCl_3$) δ 4.27 (s, 4H), 3.27 (br q, J=6.3 Hz, 8H), 1.10 (t, J=7.2 Hz, 12H). $^{13}$C {$^1$H} NMR ($CDCl_3$) δ 156.1, 63.8, 42.1 (br), 14.2 (br). IR (film) 1701; MS (thermal spray) m/z=261 (MH+).

TABLE 5

$$2 \text{ RR'NH} + 2 \text{ CO}_2 + 2 \text{ Base} \xrightarrow{\text{Cl}-(CH_2)_n-\text{Cl}} \text{RR'NCO}_2-(CH_2)_n-O_2\text{CNRR'}$$

| Ex. # | RR'NH | Base | n = | Solvent | Temp. (°C.) | % Di-urethane G.C. Yield (Compound #) | Isolated Yield |
|---|---|---|---|---|---|---|---|
| 31 | $Bu_2NH$ | CyTMG | 4 | $CH_3CN$ | 75 | —(29) | 70 |
| 32 | $Et_2NH$ | DBU | 4 | DMF[1] | 70 | 96.5(30) | — |
| 33 | $Allyl_2NH$ | DBU | 4 | $CH_3CN$ | 70 | —(31) | 88 |
| 34 | $BuNH_2$ | DBU | 4 | N—MP[2] | 85 | 44(32) | — |
| 34 | $BuNH_2$ | CyTMG | 4 | N—MP[2] | 85 | 91.5(32) | 77 |
| 35 | $Et_2NH$ | CyTMG | 2 | $CH_3CN$ | 70 | 85(33) | 45 |

All reactions were run under 160 psig carbon dioxide pressure and were run to completion based on the starting dichloride.
G.C. Yields are based on biphenyl as internal standard.
[1]DMF = N,N-dimethylformamide.
[2]N—MP = 1-methyl-2-pyrrolidinone.

The products resulting from the above-described process can be utilized to prepare polyurethanes and polycarbonates. Such products can be subjected to any one of many polymerization conditions well known in the art, depending upon the desired end use, e.g., for polyurethanes, in fibers, coatings, moulding applications and the like, and for polycarbonates, in lenses, windows, telephone parts and the like. See, for example, Mark H.; Bikales N.; Overberger C.; Menges G.; Kroschwitz J. "Encyclopedia of Polymer Science and Engineering" 2nd Ed. John Wiley & Sons, N.Y. 1985, which is hereby incorporated by reference.

In addition, living polymers can be prepared utilizing diamines, polyamines, diols, polyols or mixtures thereof and hydrocarbyl dihalides or hydrocarbylpoly(halides). Where it is desired to produce living polymers having a weight average molecular weight (Mw) of less than about 10,000, the reaction can be conducted utilizing any of the bases described above, such as the amidines or guanidines. However, where it is desired to utilize the carbamates and/or carbonates of the present invention to produce a living polymer having a Mw of greater than about 10,000, it is necessary to conduct the reaction in the presence of a base that will not react with the hydrocarbyl halide (which would act to terminate chain propagation of the polymerization reaction). That is, an organic nitrogenous base which is sufficiently sterically hindered such that reaction with the hydrocarbyl halide is minimized. A suitable test for determining whether a particular base is suitable, i.e., is sufficiently sterically hindered, is whether the base reacts with benzyl chloride under conditions which simulate the polymerization reaction of interest. Specific suitable bases for use in such polymerization reactions include the guanidine bases as previously described. Certain amidine bases are also sufficiently sterically hindered. An example of one of such amidines is t-butyl dimethyl acetamidine. The following Examples 36–39 illustrate preparation of polymer materials according to the teaching of the present invention.

EXAMPLE 36

Oligo-urethane from piperazine, carbon dioxide and 1,4-dichlorobutane (chloro terminated) (34)

A 160 cc Parr autoclave was charged with 3.44 g (0.04 mol) piperazine, 16.75 g (0.10 mol) N-cyclohexyl-N′,N′,N″,N″-tetramethylguanidine and 35 mL $CH_3CN$. The autoclave was attached to a pressure head and at room temperature with stirring was added 160 psig carbon dioxide. Addition of $CO_2$ resulted in an exothermic reaction with a rise in temperature to ca. 40° C. Into a Fischer-Porter bottle was added 5.6 g (0.044 mol) 1,4-dichlorobutane in 10 mL $CH_3CN$. This mixture was attached to a pressure head and 80 psig carbon dioxide was added above the solution. After 1 h the dichlorobutane solution was added all at once under 80 psig $CO_2$ to the pre-formed carbamate anion solution generated in the autoclave. After addition the pressure was raised to 160 psig with carbon dioxide and the reaction mixture was warmed to 70° C. for 18 h. After this time the reaction mixture was allowed to cool to room temperature and then the pressure was released. The reaction mixture was poured into 150 mL water giving a tan solid. This solid was collected by filtration, washed with water, $CH_3CN$ and diethyl ether (7.27 g, IR ($CHCl_3$) 1688. $M_n = 3390$ by NMR end group analysis.

EXAMPLE 37

Oligo-urethane from piperazine, carbon dioxide and 1,4-dichlorobutane (amine terminated) (35)

A 160 cc Parr autoclave was charged with 3.44 g (0.04 mol) piperazine, 16.75 g (0.10 mol) N-cyclohexyl-N′,N′,N″,N″-tetramethylguanidine and 35 mL $CH_3CN$. The autoclave was attached to a pressure head and at room temperature with stirring was added 160 psig carbon dioxide. Addition of $CO_2$ resulted in an exothermic reaction with a rise in temperature to ca. 40° C. Into a Fischer-Porter bottle was added 4.57 g (0.036 mol) 1,4-dichlorobutane in 10 mL $CH_3CN$. This mixture was attached to a pressure head and 80 psig carbon dioxide was added above the solution. After 1 h the dichlorobutane solution was added all at once under 80 psig $CO_2$ to the pre-formed carbamate anion solution generated in the autoclave. After addition the pressure was raised to 160 psig with carbon dioxide and the reaction mixture was warmed to 70° C. for 18 h. After this time the reaction mixture was allowed to cool to room temperature and then the pressure was released. The reaction mixture was poured into 150 mL 0.5 M aqueous NaOH giving a tan solid. This solid was collected by filtration, washed with water, $CH_3CN$ and diethyl ether (5.5 g, 64.4%). $^1H$ NMR ($CDCl_3$) δ Oligomer backbone 4.17 (m), 3.49 (s), 1.76 (m), Oligomer terminus 3.49 (shoulder), 2.86 (m). IR (CHCl$) 3321 (N—H), 1690. $M_n$ (NMR end group analysis) = 3250.

EXAMPLE 38

Chloro-terminated pre-polymer from 4,4′-methylene-bis-(cyclohexylamine), carbon dioxide and 1,4-dichlorobutane (36)

10.5 g (0.05 mole) 4,4′-methylene-bis(cyclohexylamine), 26.6 g (0.105 mole) N-cyclohexyl-N′,N′,N″,N″-tetraethyl guanidine and 40 mL 1-methyl-2-pyrrolidinone were added to a 160 cc stainless steel Parr autoclave. With stirring, 350–400 rpm, carbon dioxide pressure was added above the reaction mixture, 160 psig, (rxn is exothermic, temperature reached ca. 50° C.). After 1 h 7.62 g (0.06 mole) 1,4-dichlorobutane in 10 mL N-MP was added all at once. The inlet of $CO_2$ was shut off and the reaction mixture was allowed to stir at 85° C. for 5 h. After this time the reaction was allowed to cool to 40° C. and an additional 5 g (0.039 mole) 1,4-dichlorobutane was added to the reaction mixture. The reaction was heated to 85° C. for 14 h after which time the reaction was allowed to cool to room temperature and the pressure released. The crude reaction mixture (thick light yellow homogeneous solution) was slowly dripped into 200 ml water giving a white ppt. The ppt. was collected by filtration and washed with water, acetonitrile and finally diethyl ether. The product was dried in a vacuum oven at 60° C. IR ($CHCl_3$) 3443, 1707. $M_n$ (NMR end group analysis) = 1570.

EXAMPLE 39

Polyurethane from pre-polymer 36, carbon dioxide and Jeffamine-D-2000 (37)

A 300 cc stainless steel Parr autoclave was charged with 10 g (0.005 mol) Jeffamine-D-2000, 3.04 g (0.012 mol) N-cyclohexyl-N′, N′, N″, N″-tetraethylguanidine, 8 g (ca. 0.005 mol) of the chloro-terminated pre-polyurethane 36 and 60 mL 1-methyl-2-pyrrolidinone. The autoclave was attached to its pressure head and 160 psig of carbon dioxide was added above the reaction mixture After 1 h the mixture was heated to 105° C. for 3 d. After this period of time the reaction was allowed to cool to room temperature and the pressure released. The thick yellow solution was slowly dripped into water giving a stringy white solid. This solid was collected, washed with water and air dried. IR ($CHCl_3$) 3441, 1709. GPC analysis: $M_n = 8000$, $M_w = 17800$, $M_n M_w = 2.2$.

EXAMPLE 40

This example illustrates the base effect on generation of polymers (polyurethanes) and demonstrates that guanidine bases must be utilized to produce polyurethanes having a Mw of about 10,000 or greater. A Fischer Porter bottle was charged with 2.1 g (0.01 mol) 4,4′-methylene-bis 2 g (0.005 mol) Jeffamine-D-400, 5.02 g (0.0325 mol) ,8-diazabicyclo[ 5.4.0]undec-7-ene (DBU) and 10 mL 1-methyl-2-pyrrolidinone (N-MP). The Fischer-Porter bottle was attached to a pressure head and at room temperature with stirring was added 80 psig carbon dioxide. Addition of $CO_2$ resulted in an exothermic reaction with a rise in temperature to ca. 40° C. Into a second Fischer-Porter bottle was added 2.62 g (0.015 mol) a,a′-dichloro-p-xylene in 15 mL N-MP. This was attached to a pressure head and 80 psig carbon dioxide was added above the solution. After 1 h the dichloride solution was added all at once under 80 psig $CO_2$ to the pre-formed carbamate anion solution generated in the first Fischer-Porter bottle. After addition the reaction mixture was warmed to 55° C. for 2 d. Aliquots were taken after 1 d and 2 d. Each aliquot was dripped slowly into water and the solid collected by filtration, washed with water and air dried at room temperature. Molecular weight data was obtained by GPC-HPLC analysis and the results are given in Table 6. The above reaction was repeated using N-cyclohexyl-N',N',N'',N''-tetramethylguanidine (CyTMG) and N-cyclohexyl-N',N',N'',N''-tetraethylguanidine (CyTEG) in place of DBU. The results are given in Table 6. IR (CHCl$_3$) 3441, 1709.

$$H_2N\text{—}\langle\bigcirc\rangle\text{—}CH_2\text{—}\langle\bigcirc\rangle\text{—}NH_2 + \text{Jeffamine-D-400}^1 + CO_2 +$$

10 mmol          5 mmol          80 psig $$\text{Base} + ClCH_2\text{—}\langle\bigcirc\rangle\text{—}CH_2Cl \xrightarrow[N\text{—}MP]{55° C.}$$

33 mmol          15 mmol

| Rxn# | Base² | Rxn Time | $M_n$ | $M_w$ | $M_w/M_n$ |
|---|---|---|---|---|---|
| 1 | DBU | 1 d | 600 | 1100 | 1.83 |
|  |  | 2 d | 850 | 1750 | 2.05 |
| 2 | CyTMG | 1 d | 6050 | 13700 | 2.26 |
|  |  | 2 d | 6350 | 13000 | 2.05 |
| 3 | CyTEG | 1 d | 6800 | 13150 | 1.93 |
|  |  | 2 d | 7400 | 16300 | 2.2 |

All reactions sampled after 1 d and after 2 d and molecular weight data was obtained by GPC-HPLC using polystyrene standards. In reaction #1 (DBU) only a small amount of polymer was obtained and the molecular weight data was collected on this recovered material. In reactions #2 and #3 (CyTMG and CyTEG) good yields of recovered segmented polyurethane/polypropylene oxide resulted.
¹Jeffamine-D-400 is an amine terminated polypropylene oxide of $M_n = 400$ and was obtained from Texaco Inc.
²DBU = 1,8-diazabicyclo[5.4.0]undec-7-ene.
CyTMG = N-cyclohexyl-N',N',N'',N''-tetramethylguanidine.
CyTEG = N-cyclohexyl-N',N',N'',N''-tetraethylguanidine.

The following Examples 41–46 illustrate preparation of carbonates according to the teachings of the present invention. For comparison purposes, these reactions are summarized in Table 7.

EXAMPLE 41

Benzyl butylcarbonate (38)

A Fischer Porter bottle was charged with 1.48 g (0.02 mol) butanol, 5.3 g (0.027 mol) N-cyclohexyl-N',N',N'',N''-tetramethylguanidine and 20 mL 1-methyl-2-pyrrolidinone. The Fischer-Porter bottle was attached to a pressure head and at room temperature with stirring was added 80 psig carbon dioxide. Addition of CO$_2$ resulted in an exothermic reaction and cooling with ice was required. Into a second Fischer-Porter bottle was added 10.12 g (0.08 mol) benzyl chloride in 10 mL N-MP. This mixture was attached to a pressure head and 80 psig carbon dioxide was added above the solution. After 1 h the benzyl chloride solution was added all at once under 80 psig CO$_2$ to the pre-formed carbamate anion solution generated in the first Fischer-Porter bottle. After addition the reaction mixture was warmed to 55° C. for 18h. After this time the reaction mixture was allowed to cool to room temperature and then the pressure was released. An aliquot was taken, diluted with diethyl ether, Cl⁻ +HCyTMG filtered off, and by G.C. analysis a 90% yield of benzyl butylcarbonate was calculated. The reaction was repeated in toluene and CH$_3$CN as solvent with the results given in Table 7. The reaction was repeated using 1,8-diazabicyclo[5.4.0]undec-7-ene in place of N-cyclohexyl-N',N',N'',N'''-tetramethylguanidine with CH$_3$CN and toluene as solvent; the results are given in Table 7. Oil ¹H NMR (CDCl$_3$) 7.44–7.38 (overlapping, m 5H), 5.20 (s, 2H), 4.20 (t, J=6.7 Hz, 2H), 1.70 (m, 2H), 1.44 (m, 2H), 0.98 (t, J=7.3 Hz, 3H). ¹³C{¹H} NMR (CDCl$_3$) 155.8, 136.0, 129.0, 128.8, 69.9, 68.5, 31.2, 19.4, 14.2. IR (film) 1746, 1262.

EXAMPLE 42

Benzyl i-propylcarbonate (39)

Procedures as described in synthesis of 38. The carbonate was isolated by pouring the crude reaction mixture into diethyl ether, extracting with 2×100 mL 0.5 M aq. HCl and 1×100 mL brine, during over Na$_2$CO$_3$, filtering, concentrating and chromatography on silica gel (85%, a small amount of dibenzyl carbonate was detected and was separable from product). Oil ¹H NMR (CDCl$_3$) 7.44–7.35 (overlapping m, 5H), 5.19 (s, 2H), 4.95 (7 line pattern, J=6.3 Hz, 1H), 1.34 (d, J=6.2 Hz, 6H). ¹³C{¹H} NMR (CDCl$_3$) 155.2, 136.0, 129.1, 128.9, 128.8, 72.6, 69.7, 22.3. IR (film) 1740, 1260; MS (FAB) m/z=195 (MH+).

EXAMPLE 43

Dibenzyl carbonate (40)

Procedures as described in synthesis of 38. The car was isolated by pouring the crude reaction mixture into diethyl ether, extracting with 2×100 mL 0.5 M aq. HCl and 1×100 mL brine, during over Na$_2$CO$_3$, filtering, concentrating and chromatography on silica gel (97%). Oil ¹H NMR (CDCl$_3$) 7.45–7.35 (overlapping m, 10H), 5.25 (s, 4H). IR (film) 1746, 1262.

EXAMPLE 44

Di-ethylene glycol-bis-benzylcarbonate (41)

Procedures as described in synthesis of 38. The carbonate was isolated by pouring the crude reaction mixture into diethyl ether, extracting with 2×100 mL 0.5 M aq. HCl and 1×100 mL brine, during over Na$_2$CO$_3$, filtering, Oil ¹H NMR (CDCl$_3$) 7.43–7.34 (overlapping m, 10H) 5.20 (s, 4H), 4.33 (m, 4H), 3.74 (m, 4H). ¹³C{¹H} NMR (CDCl$_3$) 155.6, 135.7, 129.1, 129.0, 128.9, 70.2, 69.4, 67.5. 1IR (film) 1742, 1260; MS (FAB) m/z=375 (MH+). Anal. Calcd.: C, 64.16; H, 5.92. Found: C, 64.49; H, 6.19.

EXAMPLE 45

Dibutylcarbonate (42)

. A 160 cc Parr autoclave was charged with 2.22 g (0.03 mol) butanol, 6.9 g (0.035 mol) N-cyclohexyl-N',N',N'',N'''-tetramethylguanidine and 30 mL CH$_3$CN. The autoclave was attached to a pressure head and at room temperature with stirring was added 160 psig carbon dioxide. Addition of CO$_2$ resulted in an exothermic reaction with a rise in temperature to ca. 40° C. Into a Fischer-Porter bottle was added 8.33 g (0.09 mol) butyl chloride in 10 mL CH$_3$CN. This mixture was attached to a pressure head and 80 psig carbon dioxide was added above the solution. After 1 h the butyl chloride solution was added all at once under 80 psig CO$_2$ to the pre-formed carbamate anion solution generated in the autoclave. After addition the pressure was raised to 160 psig with carbon dioxide and the reaction mixture was warmed to 85° C. for 16 h. After this time the reaction mixture was allowed to cool to room temperature and then the pressure was released. An aliquot was taken, diluted with diethyl ether, Cl⁻ +HCyTMG filtered off and by G.C. analysis a 73% yield of dibutyl carbonate was calculated. Oil ¹H NMR (CDCl₃) 4.14(t, J=6.6 Hz, 4H), 1.66 (m, 4H), 1.41 (m, 4H), 0.94 (t, J=7.3 Hz, 6H). ¹³C{¹H} NMR (CDCl₃) 155.9, 68.2, 31.2, 19.4, 14.1. IR (film) 1746, 1260; MS (FAB) m/z=175 (MH+).

EXAMPLE 46

Di-ethylene glycol-bis-allylcarbonate (43)

A Fischer Porter bottle was charged with 1.06 g (0.01 mol) diethylene glycol, 5.3 g (0.027 mol) N-cyclohexyl-N',N',N'',N''-tetramethylguanidine, 154 mg biphenyl as G.C. internal standard and 20 mL CH₃CN. The Fischer-Porter bottle was attached to a pressure head and at room temperature with stirring was added 80 psig carbon dioxide. Addition of CO₂ resulted in an exothermic reaction with a rise in temperature to ca. 40° C. Into a second Fischer-Porter bottle was added 4.6 g (0.06 mol) allyl chloride in 10 mL CH₃CN. This was attached to a pressure head and 80 psig carbon dioxide was added above the solution. After 1 h the allyl chloride solution was added all at once under 80 psig CO₂ to the preformed carbamate anion solution generated in the first Fischer-Porter bottle. After addition the reaction mixture was warmed to 55° C. for 14 h. After this time the reaction mixture was allowed to cool to room temperature and then the pressure was released. An aliquot was taken, diluted with diethyl ether, Cl⁻ +HCyTMG filtered off and by G.C. analysis a yield of 84% was calculated. The crude material was poured into 100 mL diethyl ether and was then extracted with 2×100 mL 0.5 M aq. HCl and 100 mL brine. The ethereal layer was dried over Na₂CO₃, filtered and concentrated. The residue was chromatographed on silica gel using 100% hexane to remove internal standard and then CH₂Cl₂ giving 2.2 g (80%) of the di-carbonate 43. Oil ¹H NMR (CDCl₃) 5.91 (m, 2H), 5.35 (dq, J=17.2, 1.4 Hz, 2H), 5.25 (dq, J=10.4, 1.4 Hz, 2H), 4.62 (dt, J=5.8, 1.4 Hz, 4H), 4.28 (m, 4H), 3.72 (m, 4H). ¹³C{¹H} NMR (CDCl₃) 155.4, 132, 119.3, 69.4, 69.0, 67.3. IR (film) 1746, 1649, 1258.

over production in a nonpolar solvent. Similarly, carbonate production in a polar aprotic solvent is increased 100% over production in a nonpolar solvent.

Figure 1:
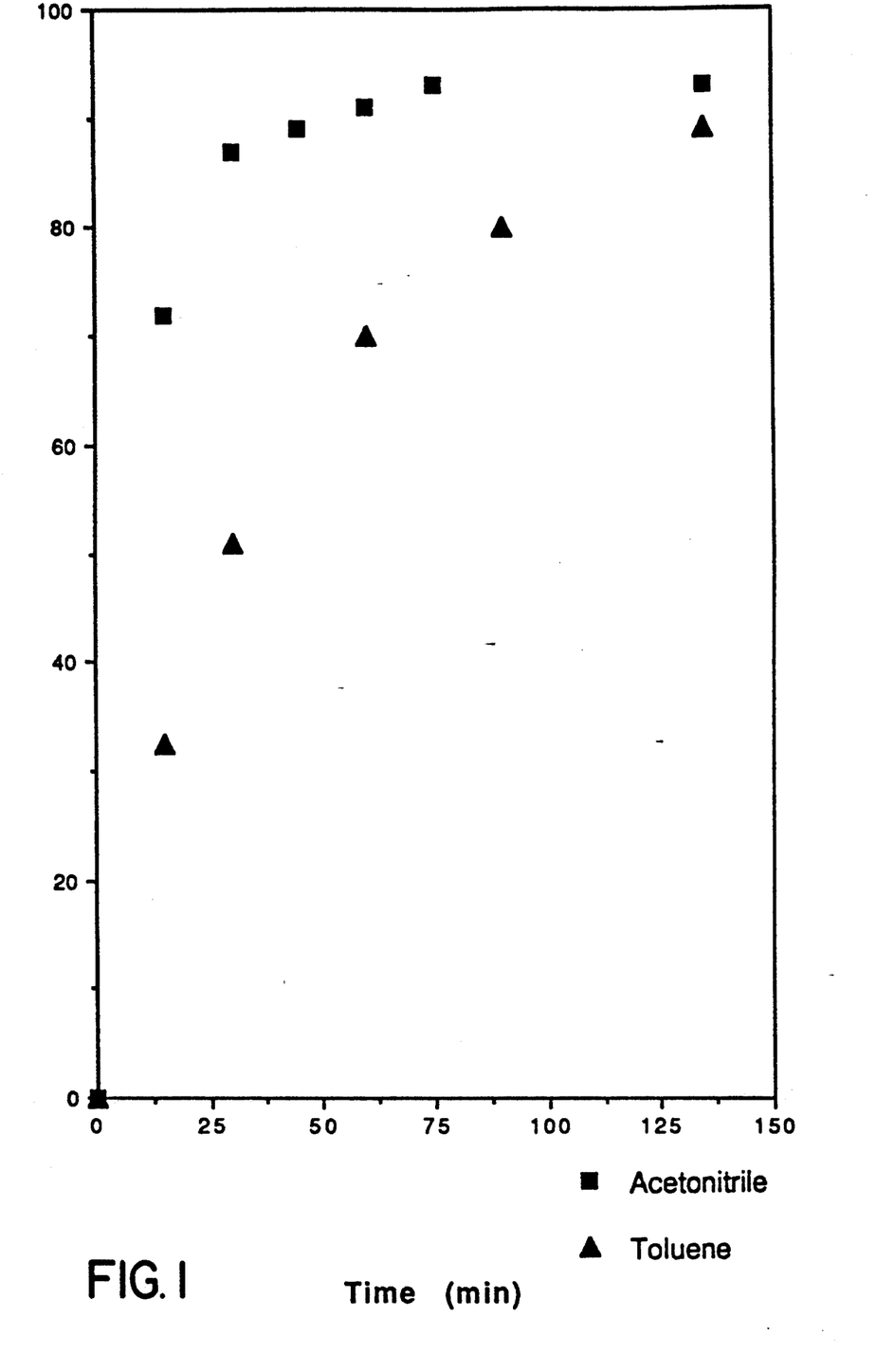
FIG. 1 is a plot of % calculated carbamic acid, benzyl ester of diethyl carbamic acid produced vs. time for reactions run in acetonitrile and toluene as described in Example 47.

Into a Fischer-Porter bottle was charged 1.46 g (0.02 mol) diethyl amine, 5.3 g (0.027 mol) N-cyclohexyl-N',N',N'',N''-tetramethylguanidine, 154 mg (0.001 mol) biphenyl as internal G.C. standard and 10 mL solvent (acetonitrile and toluene respectively). This was attached to a pressure head and 80 psig carbon dioxide added above the reaction mixture. Into a second Fischer-Porter bottle was added 10.12 (0.08 mol) benzyl chloride in 10 mL solvent. After 1 h the chloride solution was added all at once to the diethyl carbamate anion solution under 80 psig CO₂ pressure. The reaction was heated to 30° C. and monitored by G.C. A plot of % calculated carbamic acid, benzyl ester of diethyl carbamic acid produced vs. time for reactions run in acetonitrile and in toluene is shown in FIG. 1.

Figure 2:
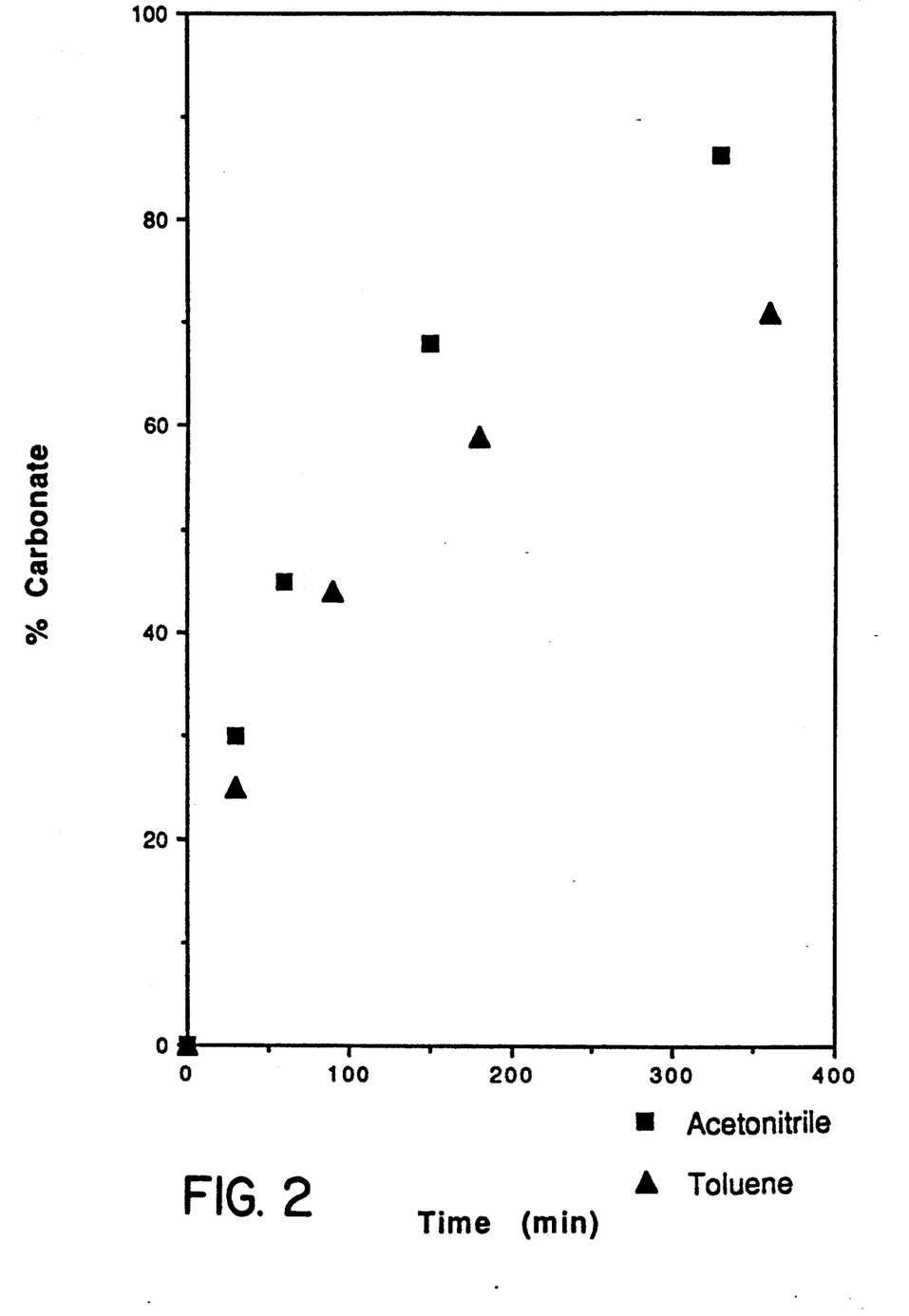
FIG. 2 is a plot of % calculated carbonic acid, phenylmethyl ester of butyl carbonic produced vs. time for reactions run in acetonitrile and toluene as described in Example 47.

Into a Fischer-Porter bottle was charged 1.48 g (0.02 mol) butanol, 5.3 g (0.027 mol) N-cyclohexyl-N',N',N'',N''-tetramethylguanidine, 154 mg (0.001 mol) biphenyl as internal G.C. standard and 10 mL solvent (acetonitrile and toluene respectively). This was attached to a pressure head and 80 psig carbon dioxide added above the reaction mixture. Into a second Fischer-Porter bottle was added 10.12 (0.08 mol) benzyl chloride in 10 mL solvent. After 1 h the chloride solution was added all at once to the diethyl carbonate anion solution under 80 psig CO₂ pressure. The reaction was heated to 30° C. and monitored by G.C. A plot of % calculated carbonic acid, phenylmethyl ester of butyl carbonic acid, 38, produced vs. time for reactings run in acetonitrile and in toluene is shown in FIG. 2.

What is claimed is:

1. A process for preparing carbonates comprising:
   (a) bringing CO₂ and an alcohol into reactive contact in the presence of a strongly basic nitrogenous compound selected from amidine and guanidine bases to form the corresponding carbonate salt, and
   (b) reacting, in a polar aprotic solvent, said salt with a primary or secondary hydrocarbyl halide.

2. The process of claim 1 wherein said polar aprotic

TABLE 7

ROH + CO₂ + Base $\xrightarrow{R'Cl}$ ROCO₂R'

| Ex. # | ROH | R'Cl | Base¹ | Solvent² | Temp. (°C.) | % Carbonate G.C. Yield (Compound #) | Isolated Yield |
|-------|-----|------|-------|----------|-------------|-------------------------------------|----------------|
| 41 | BuOH | PhCH₂Cl | CyTMG | N—MP | 55 | 90(38) | — |
| 41 | BuOH | PhCH₂Cl | CyTMG | CH₃CN | 55 | 94(38) | — |
| 41 | BuOH | PhCH₂Cl | DBU | CH₃CN | 55 | 70.5(38) | — |
| 41 | PhCH₂OH | BuCl | CyTMG | CH₃CN | 85 | 53(38) | — |
| 42 | i-PrOH | PhCH₂Cl | CyTMG | CH₃CN | 55 | —(39) | 85 |
| 43 | PhCH₂OH | PhCH₂Cl | CyTMG | CH₃CN | 55 | —(40) | 97 |
| 44 | O(CH₂CH₂OH)₂ | PhCH₂Cl | CyTMG | CH₃CN | 55 | —(41) | 76 |
| 45 | BuOH | BuCl | CyTMG | CH₃CN | 85 | 73(42) | — |
| 46 | O(CH₂CH₂OH)₂ | Ch₂=CHCH₂Cl | CyTMG | CH₃CN | 55 | 84(43) | 80 |

All reactions were run under 80–160 psig carbon dioxide pressure and carried to completion, limiting reagent = alcohol in all cases. G.C. yields determined using biphenyl as internal standard.
¹CyTMG = N-cyclohexyl-N',N',N'',N''-tetramethylguanidine. DBU = 1,8-diazabicycl[5.4.0]undec-7-ene.
²N—MP = 1-methyl-2-pyrrolidinone.

EXAMPLE 47

This example illustrates the effect on relative rate of formation of carbamate and carbonate utilizing a polar aprotic solvent according to the teachings of the present invention as opposed to a solvent as taught in *Chemistry Express* asset forth above. Thus, the rate for carbamate production in a polar aprotic solvent is increased 300% solvent is selected from the group consisting of dimethylsulfoxide, dimethylformamide, acetonitrile, N-methylpyrrolidone and mixtures thereof.

3. The process of claim 2 wherein said polar aprotic solvent is selected from the group consisting of dimethylformamide and acetonitrile.

4. The process of claim 1 wherein said primary or secondary hydrocarbyl halide is represented by the formula $R_1X$ or $XR_1X$, wherein $R_1$ represents primary or secondary radicals selected from the group consisting of alkyl, alkenyl, cycloalkyl, cycloalkenyl, aralkyl and aralkenyl radicals having 1 to about 22 carbon atoms, and X represents a halide.

5. The process of claim 4 wherein X is chloride.

6. The process of claim 1 wherein said basic nitrogenous compound is a guanidine base.

7. A process for preparing carbonates of the formula:

wherein $R_1$ represents primary or secondary radicals selected from the group consisting of alkyl, alkenyl, cycloalkyl, cycloalkenyl, aralkyl and aralkenyl radicals having 1 to about 22 carbon atoms and $R_4$ represent alkyl, alkenyl, cycloalkyl, cycloalkenyl, aralkyl, aralkenyl, alkenaryl and alkarly radicals having 1 to about 22 carbon atoms, or $R_4$ is represented by the formula:

wherein $R_5$ represents alkylene radicals having 1 to about 22 carbon atoms, and n is an integer from 0 to about 8, comprising:
 (a) bringing $CO_2$ and an alcohol into reactive contact in the presence of a strongly basic nitrogenous compound selected from amidine and guanidine bases to form the corresponding carbonate salt, and
 (b) reacting, in a polar aprotic solvent, said salt with a primary or secondary hydrocarbyl halide.

8. The process of claim 7 wherein said polar aprotic solvent is selected from the group consisting of dimethylsulfoxide, dimethylformamide, acetonitrile, N-methylpyrrolidone and mixtures thereof.

9. The process of claim 8 wherein said polar aprotic solvent is selected from the group consisting of dimethylformamide and acetonitrile.

10. The process of claim 7 wherein said primary or secondary hydrocarbyl halide is represented by the formula $R_1X$ or $XR_1X$, wherein $R_1$ represents primary or secondary radicals selected from the group consisting of alkyl, alkenyl, cycloalkyl, cycloalkenyl, aralkyl and aralkenyl radicals having 1 to about 22 carbon atoms, and X represents a halide.

11. The process of claim 10 wherein X is chloride.

12. The process of claim 7 wherein said basic nitrogenous compound is a guanidine base.

* * * * *